(12) United States Patent
Markle et al.

(10) Patent No.: US 8,738,107 B2
(45) Date of Patent: *May 27, 2014

(54) EQUILIBRIUM NON-CONSUMING FLUORESCENCE SENSOR FOR REAL TIME INTRAVASCULAR GLUCOSE MEASUREMENT

(75) Inventors: David R. Markle, Berwyn, PA (US); William Markle, Laguna Niguel, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1264 days.

This patent is subject to a terminal disclaimer.

(21) Appl. No.: 12/118,401

(22) Filed: May 9, 2008

(65) Prior Publication Data

US 2009/0018418 A1    Jan. 15, 2009

Related U.S. Application Data

(60) Provisional application No. 60/917,307, filed on May 10, 2007.

(51) Int. Cl.
    *A61B 5/1455* (2006.01)
(52) U.S. Cl.
    USPC ........................................ 600/316; 600/317
(58) Field of Classification Search
    USPC ................ 600/310, 316, 317, 322, 341, 342; 422/82.05–82.11
    See application file for complete search history.

(56) References Cited

U.S. PATENT DOCUMENTS

| 1,120,700 | A | 12/1914 | Ehrlich |
| 1,334,901 | A | 3/1920 | Higdon |
| 2,018,792 | A | 10/1935 | Kern |
| 2,094,224 | A | 9/1937 | Tietz et al. |
| 2,112,244 | A | 3/1938 | Jurist |
| 2,274,551 | A | 2/1942 | Kenyon et al. |
| 2,496,151 | A | 1/1950 | Dawson et al. |
| 2,812,524 | A | 11/1957 | Pruitt |
| 3,011,293 | A | 12/1961 | Rado |
| 3,302,219 | A | 2/1967 | Harris |
| 3,488,098 | A | 1/1970 | Sobczak |
| 3,659,586 | A | 5/1972 | Johns et al. |
| 3,685,059 | A | 8/1972 | Bokros et al. |

(Continued)

FOREIGN PATENT DOCUMENTS

| CN | 85108331 | 6/1987 |
| CS | 7707425 | 2/1980 |

(Continued)

OTHER PUBLICATIONS

Retrieved from the Internet <URL: http://www.invitrogen.com/site/us/en/home/References/Molecular-Probes-The-Handbook/Fluorophores-and-Their-Amine-Reactive-Derivatives/Fluorescein-Oregon-Green-and-Rhodamine-Green-Dyes.html#>.*

(Continued)

*Primary Examiner* — Tse Chen
*Assistant Examiner* — Chu Chuan (JJ) Liu
(74) *Attorney, Agent, or Firm* — Medtronic MiniMed, Inc.

(57) ABSTRACT

Embodiments of the present invention relates to analyte sensors. In particular, the preferred embodiments of the present invention relate to non-consuming intravascular glucose sensors based on fluorescence chemistry.

19 Claims, 15 Drawing Sheets

(56) References Cited

U.S. PATENT DOCUMENTS

| | | |
|---|---|---|
| 3,795,239 A | 3/1974 | Eberhard et al. |
| 3,827,089 A | 8/1974 | Grow |
| 3,846,353 A | 11/1974 | Grotta |
| 3,865,548 A | 2/1975 | Padawer |
| 3,874,010 A | 4/1975 | Geary |
| 3,884,225 A | 5/1975 | Witter |
| 3,895,403 A | 7/1975 | Davis |
| 3,905,888 A | 9/1975 | Mindt et al. |
| 3,909,504 A | 9/1975 | Browne |
| 3,924,281 A | 12/1975 | Gibbs |
| 3,930,580 A | 1/1976 | Bazell et al. |
| 3,996,345 A | 12/1976 | Ullman |
| 4,003,707 A | 1/1977 | Lübbers et al. |
| 4,041,932 A | 8/1977 | Fostick |
| 4,094,578 A | 6/1978 | DiVita et al. |
| 4,118,485 A | 10/1978 | Eriksson et al. |
| 4,180,879 A | 1/1980 | Mann |
| 4,197,853 A | 4/1980 | Parker |
| 4,200,110 A | 4/1980 | Peterson et al. |
| 4,240,438 A | 12/1980 | Updike et al. |
| 4,245,645 A | 1/1981 | Arseneault et al. |
| 4,269,605 A | 5/1981 | Dean et al. |
| 4,306,562 A | 12/1981 | Osborne |
| 4,307,933 A | 12/1981 | Palmer et al. |
| 4,308,254 A | 12/1981 | Tayot et al. |
| 4,344,438 A | 8/1982 | Schultz |
| 4,345,606 A | 8/1982 | Littleford |
| 4,358,851 A | 11/1982 | Scifres et al. |
| 4,361,918 A | 12/1982 | Roisaeth |
| 4,371,374 A | 2/1983 | Cerami et al. |
| 4,459,712 A | 7/1984 | Pathan |
| 4,465,335 A | 8/1984 | Eppes |
| 4,469,357 A | 9/1984 | Martin |
| 4,474,431 A | 10/1984 | Bricheno |
| 4,476,870 A | 10/1984 | Peterson et al. |
| 4,490,867 A | 1/1985 | Gabrielson |
| 4,495,293 A | 1/1985 | Shaffar |
| 4,502,169 A | 3/1985 | Persson |
| RE31,879 E | 5/1985 | Lübbers et al. |
| 4,528,616 A | 7/1985 | Koppensteiner |
| 4,548,907 A | 10/1985 | Seitz et al. |
| 4,557,900 A | 12/1985 | Heitzmann |
| 4,560,248 A | 12/1985 | Cramp et al. |
| 4,568,444 A | 2/1986 | Nakamura et al. |
| 4,579,641 A | 4/1986 | Shimomura et al. |
| 4,600,310 A | 7/1986 | Cramp et al. |
| 4,621,049 A | 11/1986 | Wang |
| 4,629,451 A | 12/1986 | Winters et al. |
| 4,636,144 A | 1/1987 | Abe et al. |
| 4,649,271 A | 3/1987 | Hök et al. |
| 4,650,472 A | 3/1987 | Bates |
| 4,654,031 A | 3/1987 | Lentz |
| 4,654,127 A | 3/1987 | Baker et al. |
| 4,654,327 A | 3/1987 | Teng |
| 4,659,817 A | 4/1987 | Gallop et al. |
| 4,675,925 A | 6/1987 | Littleton |
| 4,684,538 A | 8/1987 | Klemarczyk |
| 4,689,308 A | 8/1987 | Gerhard |
| RE32,514 E | 10/1987 | Steklenski |
| 4,703,756 A | 11/1987 | Gough et al. |
| 4,707,056 A | 11/1987 | Bittner |
| 4,710,623 A | 12/1987 | Lipson et al. |
| 4,727,730 A | 3/1988 | Boiarski et al. |
| 4,737,153 A | 4/1988 | Shimamura et al. |
| 4,744,618 A | 5/1988 | Mahlein |
| 4,746,751 A | 5/1988 | Oviatt |
| 4,750,795 A | 6/1988 | Blotekjaer |
| 4,751,918 A | 6/1988 | Bernard et al. |
| 4,754,538 A | 7/1988 | Stewart, Jr. et al. |
| 4,776,047 A | 10/1988 | DiMatteo |
| 4,785,814 A | 11/1988 | Kane |
| 4,792,689 A | 12/1988 | Peterson |
| 4,794,619 A | 12/1988 | Tregay |
| 4,796,633 A | 1/1989 | Zwirkoski |
| 4,798,738 A | 1/1989 | Yafuso |
| 4,801,187 A | 1/1989 | Elbert et al. |
| 4,803,049 A | 2/1989 | Hirschfeld et al. |
| 4,810,655 A | 3/1989 | Khalil et al. |
| 4,816,130 A | 3/1989 | Karakelle et al. |
| 4,820,636 A | 4/1989 | Hill et al. |
| 4,821,738 A | 4/1989 | Iwasaki et al. |
| 4,822,127 A | 4/1989 | Kamiya et al. |
| 4,833,091 A | 5/1989 | Leader et al. |
| 4,838,269 A | 6/1989 | Robinson et al. |
| 4,844,841 A | 7/1989 | Koller et al. |
| 4,846,543 A | 7/1989 | Kapany et al. |
| 4,851,195 A | 7/1989 | Matthews et al. |
| 4,854,321 A | 8/1989 | Boiarski |
| 4,861,728 A | 8/1989 | Wagner |
| 4,872,226 A | 10/1989 | Lonardo |
| 4,872,759 A | 10/1989 | Stich-Baumeister |
| 4,886,338 A | 12/1989 | Yafuso et al. |
| 4,889,407 A | 12/1989 | Markle et al. |
| 4,903,707 A | 2/1990 | Knute et al. |
| 4,906,232 A | 3/1990 | Reynolds |
| 4,923,273 A | 5/1990 | Taylor |
| 4,927,222 A | 5/1990 | Kamiya et al. |
| 4,937,901 A | 7/1990 | Brennan |
| 4,939,801 A | 7/1990 | Schaal et al. |
| 4,941,308 A | 7/1990 | Grabenkort et al. |
| 4,943,364 A | 7/1990 | Koch et al. |
| 4,946,038 A | 8/1990 | Eaton |
| 4,955,862 A | 9/1990 | Sepetka |
| 4,960,412 A | 10/1990 | Fink |
| 4,966,597 A | 10/1990 | Cosman |
| 5,000,901 A | 3/1991 | Iyer et al. |
| 5,005,576 A | 4/1991 | Günther |
| 5,007,704 A | 4/1991 | McCartney |
| 5,012,809 A | 5/1991 | Shulze |
| 5,018,225 A | 5/1991 | Fergni et al. |
| 5,030,420 A | 7/1991 | Bacon |
| 5,047,020 A | 9/1991 | Hsu |
| 5,047,208 A | 9/1991 | Schweitzer et al. |
| 5,047,627 A | 9/1991 | Yim et al. |
| 5,054,497 A | 10/1991 | Kapp et al. |
| 5,068,931 A | 12/1991 | Smith |
| 5,069,674 A | 12/1991 | Fearnot et al. |
| 5,082,112 A | 1/1992 | Dunklee |
| 5,093,266 A | 3/1992 | Leader et al. |
| 5,098,618 A | 3/1992 | Zelez |
| 5,104,388 A | 4/1992 | Quackenbush |
| 5,108,502 A | 4/1992 | Pawlowski et al. |
| 5,109,452 A | 4/1992 | Selvin et al. |
| 5,114,676 A | 5/1992 | Leiner |
| 5,119,463 A | 6/1992 | Vurek |
| 5,132,432 A | 7/1992 | Haugland et al. |
| 5,137,033 A | 8/1992 | Norton |
| 5,137,833 A | 8/1992 | Russell |
| 5,141,497 A | 8/1992 | Erskine |
| 5,156,962 A | 10/1992 | Suzuki et al. |
| 5,162,130 A | 11/1992 | McLaughlin |
| 5,166,990 A | 11/1992 | Riccitelli et al. |
| 5,167,715 A | 12/1992 | Kalafala et al. |
| 5,168,587 A | 12/1992 | Shutes |
| 5,175,016 A | 12/1992 | Yafuso et al. |
| 5,176,882 A | 1/1993 | Gray |
| 5,178,267 A | 1/1993 | Grabenkort et al. |
| 5,180,376 A | 1/1993 | Fischell |
| 5,182,353 A | 1/1993 | Hui et al. |
| 5,185,263 A | 2/1993 | Kroneis et al. |
| 5,188,803 A | 2/1993 | Hochberg |
| 5,217,691 A | 6/1993 | Greene et al. |
| 5,230,031 A | 7/1993 | Markle |
| 5,246,109 A | 9/1993 | Markle et al. |
| 5,246,441 A | 9/1993 | Ross et al. |
| 5,257,338 A | 10/1993 | Markle |
| 5,262,037 A | 11/1993 | Markle et al. |
| 5,279,596 A | 1/1994 | Castaneda et al. |
| 5,280,130 A | 1/1994 | Markle et al. |
| 5,280,548 A | 1/1994 | Atwater et al. |
| 5,286,294 A | 2/1994 | Ebi et al. |
| 5,290,266 A | 3/1994 | Rohling et al. |
| 5,302,731 A | 4/1994 | Pitner et al. |
| 5,305,740 A | 4/1994 | Kolobow |

(56) References Cited

U.S. PATENT DOCUMENTS

| | | |
|---|---|---|
| 5,310,471 A | 5/1994 | Markle et al. |
| 5,312,344 A | 5/1994 | Grinfeld et al. |
| 5,322,513 A | 6/1994 | Walker |
| 5,330,718 A * | 7/1994 | Hui et al. .................. 422/82.07 |
| 5,334,157 A | 8/1994 | Klein et al. |
| 5,335,305 A | 8/1994 | Kosa et al. |
| 5,354,448 A | 10/1994 | Markle et al. |
| 5,357,732 A | 10/1994 | Markle et al. |
| 5,361,758 A | 11/1994 | Hall et al. |
| 5,380,304 A | 1/1995 | Parker |
| 5,389,217 A | 2/1995 | Singer |
| 5,408,999 A | 4/1995 | Singh et al. |
| 5,409,469 A | 4/1995 | Schaerf |
| 5,503,770 A | 4/1996 | James |
| 5,511,408 A | 4/1996 | Yoshioka et al. |
| 5,511,547 A | 4/1996 | Markle et al. |
| 5,512,246 A | 4/1996 | Russell |
| 5,514,710 A | 5/1996 | Haugland et al. |
| 5,536,783 A | 7/1996 | Olstein et al. |
| 5,545,179 A | 8/1996 | Williamson, IV |
| 5,558,714 A | 9/1996 | Watanabe et al. |
| 5,569,186 A | 10/1996 | Lord et al. |
| 5,596,988 A | 1/1997 | Markle et al. |
| 5,605,152 A * | 2/1997 | Slate et al. .................. 600/316 |
| 5,618,587 A | 4/1997 | Markle et al. |
| 5,622,259 A | 4/1997 | Church |
| 5,634,911 A | 6/1997 | Hermann et al. |
| 5,643,212 A | 7/1997 | Coutre et al. |
| 5,658,264 A | 8/1997 | Samson |
| 5,669,920 A | 9/1997 | Conley et al. |
| 5,676,784 A | 10/1997 | McGaffigan |
| D388,418 S | 12/1997 | Polson et al. |
| 5,700,253 A | 12/1997 | Parker |
| 5,702,373 A | 12/1997 | Samson |
| 5,747,666 A | 5/1998 | Willis |
| 5,755,704 A | 5/1998 | Lunn |
| 5,763,238 A | 6/1998 | James |
| 5,797,876 A | 8/1998 | Spears et al. |
| 5,810,985 A | 9/1998 | Bao et al. |
| 5,827,242 A | 10/1998 | Follmer et al. |
| 5,891,100 A | 4/1999 | Fleckenstein |
| 5,891,114 A | 4/1999 | Chien et al. |
| 5,922,612 A | 7/1999 | Alder |
| 5,947,940 A | 9/1999 | Beisel |
| 5,951,929 A | 9/1999 | Wilson |
| 5,954,651 A | 9/1999 | Berg et al. |
| 6,002,954 A | 12/1999 | Van Antwerp |
| 6,011,984 A | 1/2000 | Van Antwerp |
| 6,019,736 A | 2/2000 | Avellanet et al. |
| 6,117,290 A | 9/2000 | Say et al. |
| 6,152,933 A | 11/2000 | Werp et al. |
| 6,156,010 A | 12/2000 | Kuracina et al. |
| 6,175,752 B1 | 1/2001 | Say et al. |
| 6,187,130 B1 | 2/2001 | Berard et al. |
| 6,197,534 B1 | 3/2001 | Lakowicz et al. |
| 6,200,301 B1 | 3/2001 | Pfeiffer et al. |
| 6,227,627 B1 | 5/2001 | Goossens |
| 6,254,829 B1 | 7/2001 | Hartmann et al. |
| 6,273,874 B1 | 8/2001 | Parris |
| 6,304,766 B1 | 10/2001 | Colvin, Jr. |
| 6,319,540 B1 | 11/2001 | Van Antwerp |
| 6,363,273 B1 | 3/2002 | Mastrorio et al. |
| 6,370,406 B1 | 4/2002 | Wach et al. |
| 6,375,627 B1 | 4/2002 | Mauze |
| 6,387,672 B1 | 5/2002 | Arimori et al. |
| 6,464,849 B1 | 10/2002 | Say et al. |
| 6,477,395 B2 | 11/2002 | Schulman et al. |
| 6,521,447 B2 | 2/2003 | Zou et al. |
| 6,544,212 B2 | 4/2003 | Galley et al. |
| 6,584,335 B1 | 6/2003 | Haar et al. |
| 6,585,665 B1 | 7/2003 | Chapman et al. |
| 6,602,702 B1 | 8/2003 | McDevitt et al. |
| 6,623,490 B1 | 9/2003 | Crane et al. |
| 6,627,177 B2 | 9/2003 | Singaram |
| 6,653,141 B2 | 11/2003 | Singaram |
| 6,663,595 B2 | 12/2003 | Spohn et al. |
| 6,682,938 B1 | 1/2004 | Satcher, Jr. et al. |
| 6,702,972 B1 | 3/2004 | Markle |
| 6,711,423 B2 | 3/2004 | Colvin |
| 6,741,877 B1 | 5/2004 | Shults et al. |
| 6,766,183 B2 | 7/2004 | Walsh |
| 6,794,195 B2 | 9/2004 | Colvin |
| 6,800,451 B2 | 10/2004 | Daniloff |
| 6,804,544 B2 | 10/2004 | Van Antwerp |
| 6,855,556 B2 | 2/2005 | Amiss et al. |
| 7,033,322 B2 | 4/2006 | Silver |
| 7,064,103 B2 | 6/2006 | Pitner et al. |
| D525,632 S | 7/2006 | Jost et al. |
| RE39,438 E | 12/2006 | Shah et al. |
| 7,181,260 B2 | 2/2007 | Gutierrez |
| D544,871 S | 6/2007 | Lim et al. |
| 7,226,414 B2 | 6/2007 | Ballerstadt |
| 7,229,450 B1 | 6/2007 | Chitre et al. |
| D550,242 S | 9/2007 | Niijima |
| D550,245 S | 9/2007 | Niijima |
| 7,276,029 B2 | 10/2007 | Goode, Jr. et al. |
| 7,277,740 B2 | 10/2007 | Rohleder et al. |
| 7,277,745 B2 | 10/2007 | Natarajan et al. |
| 7,303,814 B2 | 12/2007 | Lamberti et al. |
| 7,306,621 B1 | 12/2007 | Halla et al. |
| D559,264 S | 1/2008 | Niijima |
| D560,224 S | 1/2008 | Park et al. |
| 7,316,909 B2 | 1/2008 | Pitner et al. |
| 7,317,111 B2 | 1/2008 | Bhatt et al. |
| 7,326,538 B2 | 2/2008 | Pitner et al. |
| 7,345,160 B2 | 3/2008 | Daunert et al. |
| 7,353,055 B2 | 4/2008 | Hogan |
| 7,358,094 B2 | 4/2008 | Bell et al. |
| 7,381,184 B2 | 6/2008 | Funderburk et al. |
| 7,381,938 B2 | 6/2008 | Kobayashi et al. |
| 7,390,462 B2 | 6/2008 | Rao et al. |
| 7,417,164 B2 * | 8/2008 | Suri ........................ 562/31 |
| D580,950 S | 11/2008 | Steele et al. |
| D582,939 S | 12/2008 | Neuhaus |
| 7,470,420 B2 | 12/2008 | Singaram et al. |
| 7,496,392 B2 | 2/2009 | Alarcon et al. |
| D592,223 S | 5/2009 | Neuhaus |
| 7,559,894 B2 | 7/2009 | McEowen |
| 7,615,007 B2 | 11/2009 | Shults et al. |
| D610,065 S | 2/2010 | Gallert |
| 7,661,301 B2 | 2/2010 | Moor |
| 7,751,863 B2 | 7/2010 | Markle et al. |
| 7,767,846 B2 | 8/2010 | Suri |
| D626,143 S | 10/2010 | Karten et al. |
| 7,807,210 B1 | 10/2010 | Roorda et al. |
| 7,824,918 B2 | 11/2010 | Suri |
| 7,829,341 B2 | 11/2010 | Gamsey et al. |
| 7,879,024 B2 | 2/2011 | Thorstenson et al. |
| 7,881,780 B2 | 2/2011 | Flaherty |
| 7,939,664 B2 | 5/2011 | Gamsey et al. |
| 8,088,097 B2 | 1/2012 | Markle et al. |
| 8,110,251 B2 | 2/2012 | Markle et al. |
| 8,178,676 B2 | 5/2012 | Gamsey et al. |
| 8,202,731 B2 | 6/2012 | Suri |
| 8,512,245 B2 | 8/2013 | Markle et al. |
| 8,535,262 B2 | 9/2013 | Markle et al. |
| 2001/0016682 A1 | 8/2001 | Berner et al. |
| 2002/0018843 A1 | 2/2002 | Van Antwerp et al. |
| 2002/0026108 A1 | 2/2002 | Colvin, Jr. |
| 2002/0107178 A1 | 8/2002 | Van Den Berghe |
| 2002/0128546 A1 | 9/2002 | Silver |
| 2002/0193672 A1 | 12/2002 | Walsh et al. |
| 2003/0013974 A1 | 1/2003 | Natarajan et al. |
| 2003/0028089 A1 | 2/2003 | Galley et al. |
| 2003/0065254 A1 | 4/2003 | Schulman et al. |
| 2003/0100821 A1 | 5/2003 | Heller et al. |
| 2003/0171666 A1 | 9/2003 | Loeb |
| 2003/0232198 A1 | 12/2003 | Lamberti et al. |
| 2003/0232383 A1 | 12/2003 | Daunert et al. |
| 2004/0028612 A1 | 2/2004 | Singarem et al. |
| 2004/0072358 A1 | 4/2004 | Ballerstadt |
| 2004/0087842 A1 * | 5/2004 | Lakowicz et al. ............. 600/317 |
| 2004/0136924 A1 | 7/2004 | Boyd et al. |
| 2004/0176672 A1 | 9/2004 | Silver et al. |

(56) References Cited

U.S. PATENT DOCUMENTS

| | | |
|---|---|---|
| 2004/0219535 A1 | 11/2004 | Bell et al. |
| 2004/0243018 A1 | 12/2004 | Organ et al. |
| 2004/0260158 A1 | 12/2004 | Hogan |
| 2004/0260162 A1 | 12/2004 | Rohleder et al. |
| 2004/0267203 A1 | 12/2004 | Potter et al. |
| 2005/0054975 A1 | 3/2005 | Patel et al. |
| 2005/0059097 A1 | 3/2005 | Daunert et al. |
| 2005/0090014 A1 | 4/2005 | Rao et al. |
| 2005/0113658 A1* | 5/2005 | Jacobson et al. ............... 600/317 |
| 2005/0118599 A1 | 6/2005 | Pawliszyn |
| 2005/0118726 A1 | 6/2005 | Schultz et al. |
| 2005/0123935 A1 | 6/2005 | Haugland et al. |
| 2005/0124896 A1 | 6/2005 | Richter et al. |
| 2005/0130249 A1 | 6/2005 | Parris et al. |
| 2005/0193860 A1 | 9/2005 | Schulman et al. |
| 2005/0233465 A1 | 10/2005 | Miller |
| 2005/0241959 A1 | 11/2005 | Ward et al. |
| 2005/0267326 A1 | 12/2005 | Loeb et al. |
| 2005/0282225 A1 | 12/2005 | Daunert et al. |
| 2006/0008500 A1 | 1/2006 | Chavan et al. |
| 2006/0051874 A1 | 3/2006 | Reed et al. |
| 2006/0079740 A1 | 4/2006 | Silver et al. |
| 2006/0083688 A1* | 4/2006 | Singaram et al. ............... 424/9.6 |
| 2006/0084854 A1 | 4/2006 | Cho et al. |
| 2006/0088722 A1 | 4/2006 | Aller et al. |
| 2006/0105174 A1 | 5/2006 | Aller et al. |
| 2006/0173252 A1 | 8/2006 | Ellingsen et al. |
| 2006/0189863 A1 | 8/2006 | Peyser et al. |
| 2006/0189979 A1 | 8/2006 | Esch et al. |
| 2006/0195042 A1 | 8/2006 | Flaherty |
| 2006/0287600 A1 | 12/2006 | McEowen |
| 2007/0003588 A1 | 1/2007 | Chinn et al. |
| 2007/0020181 A1* | 1/2007 | Workman et al. ............... 424/9.1 |
| 2007/0060872 A1 | 3/2007 | Hall et al. |
| 2007/0100356 A1 | 5/2007 | Lucatero et al. |
| 2007/0123775 A1 | 5/2007 | Meyer et al. |
| 2007/0136825 A1 | 6/2007 | Frommer et al. |
| 2007/0156079 A1 | 7/2007 | Brown |
| 2007/0175828 A1 | 8/2007 | Goedje et al. |
| 2007/0179437 A1 | 8/2007 | Grage et al. |
| 2007/0207498 A1 | 9/2007 | Palmieri et al. |
| 2007/0256477 A1 | 11/2007 | Moor |
| 2008/0001091 A1 | 1/2008 | Kobayashi et al. |
| 2008/0009687 A1 | 1/2008 | Smith et al. |
| 2008/0027245 A1 | 1/2008 | Suri |
| 2008/0086042 A1 | 4/2008 | Brister et al. |
| 2008/0154107 A1 | 6/2008 | Jina |
| 2008/0183061 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0261255 A1 | 10/2008 | Tolosa et al. |
| 2008/0287761 A1 | 11/2008 | Hayter et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0311675 A1 | 12/2008 | Thomas et al. |
| 2008/0312560 A1 | 12/2008 | Jamsen et al. |
| 2008/0319286 A1 | 12/2008 | Ridder et al. |
| 2009/0005266 A1 | 1/2009 | Ostermeier et al. |
| 2009/0018418 A1 | 1/2009 | Markle et al. |
| 2009/0018426 A1 | 1/2009 | Markle et al. |
| 2009/0048430 A1 | 2/2009 | Hellinga et al. |
| 2009/0061528 A1 | 3/2009 | Suri |
| 2009/0062696 A1 | 3/2009 | Nathan et al. |
| 2009/0076336 A1 | 3/2009 | Mazar et al. |
| 2009/0081803 A1 | 3/2009 | Gamsey et al. |
| 2009/0082566 A1 | 3/2009 | Mitra |
| 2009/0088329 A1 | 4/2009 | Brennan et al. |
| 2009/0104714 A1 | 4/2009 | Thomas et al. |
| 2009/0112075 A1 | 4/2009 | Klok et al. |
| 2009/0143659 A1 | 6/2009 | Li et al. |
| 2009/0171381 A1 | 7/2009 | Schmitz et al. |
| 2009/0177143 A1 | 7/2009 | Markle et al. |
| 2009/0182217 A1 | 7/2009 | Li et al. |
| 2009/0192416 A1 | 7/2009 | Ernst et al. |
| 2009/0196864 A1 | 8/2009 | Bulla |
| 2009/0200620 A1 | 8/2009 | Omura et al. |
| 2009/0228068 A1 | 9/2009 | Buhlmann et al. |
| 2009/0264719 A1 | 10/2009 | Markle et al. |
| 2009/0324945 A1 | 12/2009 | Licht et al. |
| 2010/0173065 A1 | 7/2010 | Michal et al. |
| 2010/0274110 A1 | 10/2010 | Markle |
| 2010/0279424 A1 | 11/2010 | Suri |
| 2010/0292617 A1 | 11/2010 | Lei et al. |
| 2010/0312483 A1 | 12/2010 | Peysr |
| 2011/0077477 A1 | 3/2011 | Romey |
| 2011/0105866 A1 | 5/2011 | Markle |
| 2011/0152658 A1 | 6/2011 | Peyser |
| 2011/0171742 A1 | 7/2011 | Gamsey |
| 2011/0224516 A1 | 9/2011 | Romey et al. |
| 2011/0236989 A1 | 9/2011 | Suri et al. |
| 2011/0263953 A1 | 10/2011 | Markle |
| 2012/0053427 A1 | 3/2012 | Markle |
| 2012/0116191 A1 | 5/2012 | Markle |
| 2012/0208286 A1 | 8/2012 | Gamsey et al. |
| 2012/0282412 A1 | 11/2012 | Markle |
| 2013/0267801 A1 | 10/2013 | Romey |
| 2013/0267802 A1 | 10/2013 | Markle |
| 2013/0287631 A1 | 10/2013 | Romey |

FOREIGN PATENT DOCUMENTS

| | | |
|---|---|---|
| DE | 3036868 | 5/1982 |
| DE | 3509262 | 10/1985 |
| DE | 3720736 | 1/1989 |
| DE | 195 02 183 | 8/1996 |
| DE | 298 17 986 | 2/1999 |
| DE | 198 20 808 | 11/1999 |
| EP | 0 073 558 | 3/1983 |
| EP | 0 147 168 | 7/1985 |
| EP | 0 596 700 | 5/1994 |
| EP | 0 617 977 A1 | 10/1994 |
| EP | 0 758 451 B1 | 1/1999 |
| EP | 000760723-0001 | 7/2007 |
| EP | 2 162 057 | 3/2010 |
| EP | 2217316 | 7/2010 |
| EP | 2 222 686 | 8/2010 |
| EP | 2 147 003 | 4/2011 |
| EP | 2 054 476 | 6/2011 |
| EP | 2 438 152 | 4/2012 |
| EP | 2 483 679 | 8/2012 |
| EP | 2 496 139 | 9/2012 |
| EP | 2 545 373 | 1/2013 |
| FR | 2 350 831 | 12/1977 |
| FR | 2 624 007 | 6/1989 |
| GB | 1 123 094 | 8/1968 |
| GB | 1 447 163 | 8/1976 |
| GB | 2 048 682 | 12/1980 |
| JP | 53-68249 | 6/1978 |
| JP | 54-13347 | 1/1979 |
| JP | 54-111363 | 8/1979 |
| JP | 54-155856 | 12/1979 |
| JP | 56-116752 | 9/1981 |
| JP | 56-116754 | 9/1981 |
| JP | 58-162921 | 9/1983 |
| JP | 3-52936 | 3/1991 |
| JP | 06-016859 | 4/1994 |
| JP | 06-285049 | 10/1994 |
| JP | 2003-262613 | 9/2003 |
| JP | 1332866 | 5/2008 |
| JP | 2009-544729 | 12/2009 |
| JP | 2010-507711 | 3/2010 |
| JP | 2010-517693 | 5/2010 |
| JP | 2010-518397 | 5/2010 |
| JP | 2010-526599 | 8/2010 |
| JP | 2010-527010 | 8/2010 |
| JP | 2010-535903 | 11/2010 |
| JP | 2011-504399 | 2/2011 |
| JP | 2011-511755 | 4/2011 |
| JP | 5017377 | 6/2012 |
| JP | 2012-529060 | 11/2012 |
| SU | 621624 | 8/1978 |
| WO | WO 87/00920 | 2/1987 |

(56) References Cited

FOREIGN PATENT DOCUMENTS

| | | |
|---|---|---|
| WO | WO 88/04415 | 6/1988 |
| WO | WO 91/09312 | 6/1991 |
| WO | WO 92/19150 | 11/1992 |
| WO | WO 94/10553 | 5/1994 |
| WO | WO 95/30148 | 11/1995 |
| WO | WO 96/22730 | 8/1996 |
| WO | WO 96/22798 | 8/1996 |
| WO | WO 97/20530 | 6/1997 |
| WO | WO 97/37713 | 10/1997 |
| WO | WO 97/48437 | 12/1997 |
| WO | WO 98/08554 | 3/1998 |
| WO | WO 00/02048 | 1/2000 |
| WO | WO 00/13003 | 3/2000 |
| WO | WO 00/43536 | 7/2000 |
| WO | WO 01/20019 | 3/2001 |
| WO | WO 01/60248 | 8/2001 |
| WO | WO 02/46752 | 6/2002 |
| WO | WO 03/034047 | 4/2003 |
| WO | WO 03/060464 | 7/2003 |
| WO | WO 2004/072358 | 4/2004 |
| WO | WO 2004/054438 | 7/2004 |
| WO | WO 2004/099778 | 11/2004 |
| WO | WO 2005/090014 | 4/2005 |
| WO | WO 2005/054831 | 6/2005 |
| WO | WO 2005/065241 | 7/2005 |
| WO | WO 2006/023725 | 3/2006 |
| WO | WO 2006/044973 | 4/2006 |
| WO | WO 2007/059311 | 5/2007 |
| WO | WO 2007/067743 | 6/2007 |
| WO | WO 2007/105140 | 9/2007 |
| WO | WO 2008/001091 | 1/2008 |
| WO | WO 2008/014280 | 1/2008 |
| WO | WO 2008/072338 | 6/2008 |
| WO | WO 2008/097747 | 8/2008 |
| WO | WO 2008/098011 | 8/2008 |
| WO | WO 2008/098087 | 8/2008 |
| WO | WO 2008/137604 | 11/2008 |
| WO | WO 2008/141241 | 11/2008 |
| WO | WO 2008/141243 | 11/2008 |
| WO | WO 2009/009756 | 1/2009 |
| WO | WO 2009/018426 | 1/2009 |
| WO | WO 2009/021057 | 2/2009 |
| WO | WO 2009/067626 | 5/2009 |
| WO | WO 2009/129186 | 10/2009 |
| WO | WO 2010/141888 | 9/2010 |
| WO | WO 2010/123972 | 10/2010 |
| WO | WO 2010/141888 | 12/2010 |
| WO | WO 2011/041546 | 4/2011 |
| WO | WO 2011/056274 | 5/2011 |
| WO | WO 2011/075710 | 6/2011 |
| WO | WO 2011/075711 | 6/2011 |
| WO | WO 2011/084713 | 7/2011 |
| WO | WO 2011/097586 | 8/2011 |
| WO | WO 2011/112030 | 9/2011 |
| WO | WO 2011/137178 | 11/2011 |
| WO | WO 2013/033076 | 3/2013 |
| WO | WO 2013/049068 | 4/2013 |

OTHER PUBLICATIONS

Niu C.G. et al. 2005 *Anal. Bioanal. Chem* 383(2):349-357.
Turner N.G. et al. 1998 *J. Investig. Dermatol. Symp. Proc.* Aug. 3(2): 110-3.
Badugu R. et al. 2005 *Talanta* 65 (3): 762-768.
Badugu R. et al. 2005 *Talanta* 66:569-574.
Badugu R. et al 2005 Bioorg. Med. Chem 13 (1):113-119.
Xu, Z., A. Rollins, et al. (1998) "A novel fiber-optic pH sensor incorporating carboxy SNAFL-2 and fluorescent wavelength-ratiometric detection" Journal of Biomedical Materials Research 39:9-15.
Song, A., S. Parus, et al. (1997) "High-performance fiber-optic pH microsensors for practical physiological measurements using a dual-emission sensitive dye" Analytical Chemistry 69: 863-867.
Wolfbeis, O.S., E. Fuerlinger, et al. (1983) "Fluorimetric analysis. I. Study on fluorescent indicators for measuring near neutral ('physiological') pH values." Fresneius' S. Anal. Che. 314(2):119-124.
Agayn, V. I. and Dr. R. Walt (1993). "Fiber-optic sensor for continuous monitoring of fermentation pH." Biotechnology 76(6):6-9.
Lutty, G.A. (1978). "The acute intravenous toxicity of stains, dyes, and other fluorescent substances." Toxical Pharmacol. 44:225-229.
Zhujun, Z. and W.R. Seitz (1984). "A fluorescence sensor for quantifying pH in the range from 6.5 to 8.5." Analytical Chimica Acta 160: 47-55.
Offenbacher, H., O.S. Wolfbeis, et al. (1986). "Fluorescence optical sensors for continuous determination of near-neutral pH values." Sensor Actuator 9: 73-84.
Schulman, S.G., S. Chen, et al. (1995). "Dependence of the fluorescence of immobilized 1-hydroxypyrene-3,6,8-trisulfonate on solution pH: extension of the range of applicability of a pH fluorosensor."
Gehrich, J. L., D.W. Lubbers, et al. (1986). "Optical fluorescence and its application to an intravascular blood gas monitoring system." IEE TBio-med Eng BME-33: 117-132.
Zhang, S., S. Tanaka, et al. (1995). "Fibre-optical sensor based on fluorescent indicator for monitoring physiological pH values." Med Biol Eng Comput 33: 152-156.
Kostov, Y., P. Harms, et al. (2001). "Low-cost microbioreactor for high-throughput bioprocessing." Biotechnol Bioeng 72:346-352.
The Immunoassay Handbook, pp. 1-618, ed. David Wild, Macmillan Press, 1994, United Kingdom.
Meadows and Schultz (1993) Anal. Chim. Acta 280: pp. 21-30.
Lakowitz et al., Analytica Chimica Acta, 271, (1993), 155-164.
PCT International Search Report for App. No. PCT/US 2008/63330 dated Sep. 3, 2008.
PCT Application No. PCT/US2008/063332, Application and Drawings.
PCT Application No. PCT/US2008/063330, Application and Drawings.
"Optical Glucose Sensor Holds Promise for Diabetics and Intensive Care Patients," in Science Daily, Mar. 18, 2004 (archived on Apr. 4, 2004 at: <http://web.archive.org/web/20040404161607/http://www.ScienceDaily.com/releases/2004/03/0403529.htm> ("ScienceDaily Article").
Atherton, S. J., et al.: "Reactions of Three Bis(viologen) Tetraquaternary Salts and Their Reduced Radicals", J. Am. Chem. Soc. 1986, 108, 3380-3385.
Cao, H., et al.: "Fluorescent Chemosensors for Carbohydrates: A Decade's Worth of Bright Spies for Saccharides in Review", Journal of Fluorescence, vol. 14, No. 5, Sep. 2004.
Cappuccio, F.E. et al. 2004 "Evaluation of pyranine derivatives in boronic acid based saccharide sensing: Significance of charge interaction between dye and quencher in solution and hydrogel" Journal of Fluorescence 14:521-533.
Check, William, "ICUs tighten belts on blood glucose levels," in Cap Today, vol. 14, No. 2, Feb. 2005, pp. 1, 95-96, 98, 100, 102, and 104 ("Check").
Cordes, D. B., et al.: "The Interaction of Boronic Acid-Substituted Viologens with Pyranine: The Effects of Quencher Charge on Fluorescence Quenching and Glucose Response", Langmuir 2005, 21, 6540-6547.
Cordes, D.B., et al.: "Two-component optical sugar sensing using boronic acid-substituted viologens with anionic fluorescent dyes-Modulated quenching with viologens as a method for monosaccharide detection", Topics in Fluorescence Spectroscopy: vol. 11, Glucose Sensing 2006, Springer, pp. 47-87 (ISBN: 978-0-387-29571-8 p. 76, scheme 3.7).
DiCesare, N., et al.: "Saccharide Detection Based on the Amplified Fluorescence Quenching of a Water-Soluble Poly(phenylene ethynylene) by a Boronic Acid Functionalized Benzyl Viologen Derivative", Langmuir 2002, 18, 7785-7787.
EPO Exam Report re EP App. No. 08 728 399.0, dated Dec. 7, 2010.
EPO Office Action re App. No. 07 799 791.4 dated Jan. 29, 2010.
European Examination dated Apr. 1, 2010, re EP Application No. 08 769 266.1-1211.
European Examination Report dated Jan. 25, 2012, re EP Application No. 08 729 209.0.
European Examination Report dated Jul. 2, 2012, re EP Application No. 08 729 209.0.

(56) References Cited

OTHER PUBLICATIONS

European Examination Report dated May 11, 2010, re EP Application No. 08 729 209.0.
European Examination Report re App. No. 08 797 302.0, dated Jan. 24, 2011.
European Examination Report re App. No. 08 797 302.0, dated Nov. 7, 2011.
European Examination Report re Application No. 08 755 267.5, dated Apr. 26, 2010.
European Examination Report re Application No. 08 755 267.5, dated Sep. 14, 2010.
Furnary et al., "Effect of hyperglycemia and continuous intravenous insulin infustions on outcomes of cardiac surgical procedures: the Portland Diabetic project," in Endocrine Practice, vol. 10 (Supp. 2), 21-33 (Mar./Apr. 2004) ("Furnary Paper (2004)").
Gamsey, S. et al. 2007 "Boronic acid based bipyridinium salts as tunable receptors for monosaccharides and alpha-hydroxycarboxylates" J Am Chem Soc 129:1278-1286.
Gamsey, Soya et al.: "Continuous glulcose detection using boronic acid-substituted viologens in fluorescent hydrogels: linker effects and extension to fiber optics" Langmuir, ACS, Washington, DC vol. 22, No. 21, Oct. 10, 2006, pp. 9067-9074 (XP002442273 ISSN: 0743-7463, compound (1) schemata 1,2 figure 1).
Hirata O. et al. 2002 "Allosteric saccharide sensing by a phenylboronic-acids-appended 5,15-bis(triarylethynyl)porphyrin" J Supramolecular Chemistry 2:133-142.
Hvastkovs, E. G., et al.: "Minor Groove Binding of a Novel Tetracationic Diviologen", Langmuir 2006, 22, 10821-10829.
International Preliminary Report and Written Opinion of the International Searching Authority for International Application No. PCT/US2009/040379 issued on Oct. 19, 2010.
International Search Report and Written Opinion of the International Searching Authority for International Application No. PCT/US10/50910, dated Dec. 3, 2010.
International Search Report and Written Opinion of the International Searching Authority for International Application No. PCT/US10/61163 mailed on Mar. 9, 2011.
International Search Report and Written Opinion of the International Searching Authority for International Application No. PCT/US10/61169 mailed on Mar. 1, 2011.
International Search Report and Written Opinion of the International Searching Authority for International Application No. PCT/US2008/053097 mailed on Jun. 27, 2008.
International Search Report and Written Opinion of the International Searching Authority for International Application No. PCT/US2010/037502 mailed on Aug. 6, 2010.
International Search Report and Written Opinion of the International Searching Authority for International Application No. PCT/US2010/044761 mailed on Oct. 6, 2010.
International Search Report and Written Opinion of the International Searching Authority for International Application No. PCT/US2011/023939 mailed on Jul. 27, 2011.
International Search Report and Written Opinion of the International Searching Authority for International Application No. PCT/US2011/028222 mailed on May 6, 2011.
International Search Report and Written Opinion of the International Searching Authority for International Application No. PCT/US2011/034167 mailed on Jul. 29, 2011.
International Search Report for International Application No. PCT/US10/61173 mailed on Feb. 28, 2011.
Japanese First Office Action, re JP Application No. 2009-549167, dated Nov. 29, 2011.
Japanese Office Action, re JP Application No. 2009-521962, dated Jul. 31, 2012.
Japanese Office Action, re JP Application No. 2009-549225, mailed Sep. 4, 2012.
Japanese Office Action, re JP Application No. 2010-507712, dated Jun. 15, 2012.
Kuwabara, T., et al.: "Effect of Alkali Metal Ions on Photochromic Behavior of Bisviologen-incorporated Oligo-oxyethylene Units", Rapid Communication. Photochemistry and Photobiology, 2003, 77(5); 572-575.
Lee, S. K., et al.: "Conformation and binding properties of polymethylene-linked bisviologens-2-naphthol complexes", Journal of the Chemical Society, Perkin Transactions 2 2001, 1983-1988.
Levetan et al., "Hospital Management of Diabetes," in Acute Complications of Diabetes, vol. 29, No. 4, 745-71, at 745-54 (Dec. 2000) ("Levetan Paper (2000)").
Mohr, G. J. et al.: Application of a Novel Lipophilized Fluorescent dye in an Opitcal Nitrate Sensor, Journal of Fluorescence 1995, 5, 135-138.
Office Action issued in European Patent Application No. 07799791.4 on Jan. 29, 2010.
Office Action issued in European Patent Application No. 08728399.0 on Dec. 7, 2010.
Office Action issued in European Patent Application No. 08755267.5 on Sep. 14, 2010.
Office Action issued in European Patent Application No. 08797302.0 on Jan. 24, 2011.
Office Action issued in European Patent Application No. 08797302.0 on Nov. 7, 2011.
Office Action issued in European Patent Application No. 08729209.0 on Jan. 25, 2012.
Office Action issued in Japanese Patent Application No. 2009-549167 on Nov. 29, 2011.
Park, Y. S., et al.: "Facile Reduction of Zeolite0Encapsulated Viologens with Solvated Electrons and Selective Dispersion of Inter- and Intramolecular Dimers of Propylene-Bridged Bisviologen Radical Cation", Langmuir 2000, 16, 4470-4477.
Partial International Search Report for International Application No. PCT/US2008/053226 mailed on Jun. 27, 2008.
PCT Application No. PCT/US2008/063330; [WO 2008/141241].
PCT Application No. PCT/US2008/063332; [WO 2008/141243].
PCT International Preliminary Report and Written Opinion re PCT/US2009/040379 dated Oct. 19, 2010.
PCT International Preliminary Report on Patentabilitu re PCT/US2008/063330 dated Nov. 19, 2009.
PCT International Preliminary Report on Patentability and Written Opinion date of Issuance Apr. 3, 2012.
PCT International Preliminary Report on Patentability and Written Opinion re PCT Application No. PCT/US2010/061169, dated Jun. 19, 2012.
PCT International Preliminary Report on Patentability and Written Opinion re PCT Application No. PCT/US2010/061173, dated Jun. 19, 2012.
PCT International Preliminary Report on Patentability and Written Opinion re PCT/US2008/053097 dated Aug. 11, 2009.
PCT International Preliminary Report on Patentability and Written Opinion re PCT/US2008/072359, dated Feb. 9, 2010.
PCT International Search Report (Declaration of Non-Establishment of ISR) and Written Opinion re PCT/US2009/040379 dated Aug. 4, 2009.
PCT International Search Report and Report on Patentability re PCT Application No. PCT/US2010/061163, dated (mailed) Jun. 28, 2012.
PCT International Search Report and Written Opinion in App. No. PCT/US2011/028222, dated May 6, 2011, in 30 pages.
PCT International Search Report and Written Opinion re App. No. PCT/US 10/61163, dated Mar. 9, 2011.
PCT International Search Report and Written Opinion re App. No. PCT/US10/61169, dated Mar. 1, 2011.
PCT International Search Report and Written Opinion re App. No. PCT/US10/61173, dated Feb. 28, 2011.
PCT International Search Report and Written Opinion re PCT App. No. PCT/US 10/50910, dated Dec. 3, 2010.
PCT International Search Report and Written Opinion re PCT/US2008/052204, dated May 27, 2008.
PCT International Search Report and Written Opinion re PCT/US2008/053226, dated Oct. 15, 2008.
PCT International Search Report and Written Opinion re PCT/US2008/069855 dated Apr. 16, 2009.

(56) References Cited

OTHER PUBLICATIONS

PCT International Search Report and Written Opinion re PCT/US2008/072359 dated Dec. 15, 2008.
PCT International Search Report and Written Opinion re PCT/US2008/084239 dated Jan. 29, 2009.
PCT International Search Report and Written Opinion re PCT/US2010/037502, dated Aug. 6, 2010.
PCT International Search Report and Written Opinion re PCT/US2010/044761, dated Oct. 6, 2010.
PCT International Search Report and Written Opinion re PCT/US2011/034167, mailed Jul. 29, 2011.
PCT International Search Report re PCT/US2007/074255 dated Jul. 8, 2008 in 3 pages.
PCT Partial International Search Report re PCT/US2008/072359 dated Oct. 15, 2008.
PCT Partial Search Report re PCT/US2008/053226 dated Jun. 27, 2008.
PCT Preliminary Report re PCT/US2008/084239 dated May 25, 2010.
PCT Report on Patentability and Written Opinion re PCT/US2007/074255 dated Jan. 27, 2009 in 9 pages.
PCT Report on Patentability and Written Opinion re PCT/US2008/063332 dated Nov. 19, 2009.
PCT Search Report and Written Opinion re PCT/US2011/023939, dated Jul. 27, 2011.
Sato, H., et al.: "Polymer Effect in Electrochromic Behavior of Oligomeric Viologens", Journal of Applied Polymer Science, vol. 24, 2075-2085 (1979).
Sharrett, Z. et al. 2008 "Boronic acid-appended bis-viologens as a new family of viologen quenchers for glucose sensing" Tetrahedron Letters 49:300-304.
Sturdevant, M. F.: "How Sterilization Changes Long-Term Resin Properties", Plastics Engineering, Jan. 1991, pp. 27-32.
Suri, J. T. et al. 2003 "Continuous glucose sensing with a fluorescent thin-film hydrogel" Angew Chem Int Ed 42:5857-5859.
Suri, J. T. et al.: "Monosaccharide Detection with 4,7-Phenanthrolinium Salts: Charge-Induced Fuorescence Sensig", Langmuir 2003, 19, 5145-5152.
Takashima, H., et al.: "Remarkably stereoselective photoinduced electron-transfer reaction between zinc myoglobin and optically active binaphthyl bisviologen", Journal o Biological Inorganic Chemistry 2003, 8, 499-506.
Tsukahara, K., et al.: "Syntheses, Characterizations, and Redox Behavior of Optically Active Viologens and Bisviologens", Bulletin of the Chemical Society of Japan 1999, 72, 139-149.
U.S. Reexamination, Request for Inter Partes Reexamination, dated Sep. 6, 2012.
Van den Berghe et al., "Intensive insulin therapy in critically ill patients," in The New England Journal of Medicine, vol. 345, No. 19, pp. 1359-1369, (Nov. 8, 2001) ("Van den Berghe Paper (2001)").
Wang, D. et al. 2001 "Photoluminescence quenching of conjugated macromolecules by bipyridinium derivatives in aqueous media: charge dependence" Langmuir 17:1262-1266.
Wilson et al., "Intensive insulin therapy in crital care: A review of 12 protocols," in Diabetes Care, vol. 30, No. 4, pp. 1005-1011 (Apr. 2007) ("Wilson Paper (2007)").
U.S. Transmittal of Communication toThird Party Requste Inter Partes Reexamination dated Oct. 22, 2012.
Angel, S. M., "Optrodes: Chemically Selective Fiber Optic Sensors," Spectroscopy, Apr. 1987, pp. 38-47.
Ayala et al., Database Caplus, DN 133:189758. (Protein Science (2000), 9(8), 1589-1593).
Badugu, R., et al.: "A Glucose sensing contact lens: A new approace to non-invasive continuous physiological glucose monitoring", SPIE Proceedings, The International Society for Optical Engineering—SPIE, Bellingha, Washington, USA, vol. 5317, Jan. 25, 2004.
Baldini "Invasive Sensors in Medicine." Optical Chemical Sensors, NATO Science Series 11: Mathematics, Physics and Chemistry [online], 2006 [Retrieved on Nov. 15, 2010], vol. 224, pp. 417-435, Retrieved from the Internet: <URL http:www.springerlink.com>.

Ballerstadt, Ralph, et al.: "Fluorescence Resonance Energy Transfer-Based Near-Infrared Fluorescence Sensor for Glucose Monitoring", Diabetes Technology & Therapeutics, vol. 6, No. 2, Apr. 1, 2004.
Bean & Johnson, 54 J. Am. Chem. Soc. 4415 (1932).
Benmakroha et al. "Haemocompatibility of invasive sensors," Med. & Biol. Eng. & Comput., 1995, 33,811-821 (Nov. 1995).
Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495.
Burnett, Peebles & Hageman, 96 Biochemical and Biophysical Research Communications 157 (1980).
Choleau et al.: "Calibration of a subcutaneous amperometric glucose sensor implanted for 7 days in diabetic patients, Part 2. Superiority of the one-point calibration method." Biosensors and Bioelectrics, vol. 17, No. 8, Aug. 1, 2002.
Dawson, et al., 98 JACS 5996 (1970).
Definition of "cathether" from Webster's Ninth New Collegiate Dictionary, 1990, p. 216.
English Translation of DE 3,720,736.
European Supplementary Search Report, re EP Application EP 10 78 4194, dated Nov. 8, 2012.
"Fiber Optic Oxygen Sensors: Theory of Operation", Fiber Optic Oxygen Sensors Theory of Operation, http://www.oceanoptics.com/Products/sensortheory.asp—4 pages.
Fidaleo et al., Database Caplus, DN 140:249134 (Chemical and Biochemical Engineering Quarterly (2003), 17(4), 311-318).
Forster, "Intermolecular Energy Transfer and Fluorescence, Annaten der Physik" (1948) pp. 55-75.
Gamoh, et al., 222 Analytica Chimica Acta 201 (1989).
Glazer, "The Time-Dependent Specific Interaction of 4-(4'-Aminophenylazo)Phenylarsonic Acid with Subtilisins," 59 Biochemistry 996 (1968).
Glazer, Chemical Abstracts, vol. 68, No. 23, Jun. 3, 1968, p. 111809 (total 3 pages).
Guilbault, George E., "Practical Fluorescence" (1973), pp. 599-600.
Hakkinen, Lajunen & Purokoski, A Potentiometric Study on the Complex Formation of Lactitol and Maltitol with Some Inorganic Oxyacids in Aqueous Solution, Chemical Abstracts, vol. 110, No. 83116f (1989).
Hakkinen, Purokoski & Lajunen, A Potentiometric Study on the Complex Formation of Germanic Acid and Germanate Ion with Sugar Acids and Disaccharides in Aqueous Solution, Chemical Abstracts, vol. 105, No. 233265s (1986).
Hayashi, et al., "Fluorometric measurement of glycosylated albumin in human serum," 149 Clinica Chimica Acta 149 (1985), 13-19 Elsevier.
Hirsch IRL B. et al. "Acute Complications of Diabetes" Endocrinology and Metabolism Clinics of North America, Dec. 2000, pp. 745-771, vol. 29-4.
Hirshfeld, "Reabsorption Sensing in Fluorescence Spectroscopy," UCRL Abstract No. 89736 Abst, published by Pittsberg Conference on Scientific Instrumentation, Mar. 1984.
Kuraganov, B. I., et al.: "Criterion for Hill equation validity for description of biosensor calibration curves", Analytica Chimica Acta, vol. 427, No. 1, Jan. 1, 2001.
Leijten FSS & De Weerdt A W 1994 Critical illness polyneuropathy: a review of the literature, definition and pathophysiology. Clinical Neurology and Neurosurgery, 96: 10-19.
Lindner, et al., 473 J. Chromatography 227-240 (1989).
Liu, et al., "Characterization of Immobilization of an Enzyme in a Modified Y Zeolite Matrix and Its Application to an Amperometric Glucose Biosensor," Anal. Chem. 1997, 69, pp. 2343-2348.
Medtronic, Features of the Guardian Real-Time Continuous Glucose Monitoring System, Features that fit your diabetes management lifestyle, located at http://www.minimed.com/products/guardian/features.html on Aug. 28, 2007.
Mignani et al. "Biomedical sensors using optical fibres." Reports on Progress in Physics [online], Jan. 1996 [Retrieved on Nov. 15, 2010], vol. 59, No. 1, pp. 1-28, Retrieved from the internet: <URL http//iopscience.iop.org>.
Mizock B A. Am J Med 1995; 98: 75-84.
Mosbach, Methods in Enzymology, vol. XLIV, 53 (1976).

(56) References Cited

OTHER PUBLICATIONS

PCT Partial International Search Report re PCT/US2008/063332 dated Oct. 20, 2008.
PCT International Search Report and Written Opinion re PCT/US2008/062303 dated Aug. 14, 2008.
PCT International Report on Patentability re PCT/US2010/044761, dated May 9, 2012.
PCT International Preliminary Report on Patentability re PCT/US2010/037502, dated Dec. 6, 2011.
PCT International Search Report and Written Opinion in App. No. PCT/US2011/028222, dated Sep. 20, 2012, in 19 pages.
PCT International Preliminary Report on Patentability re PCT/US2011/034167, issued Oct. 30, 2012.
Piper, Hannah G. "Real-Time Continuous Glucose Monitoring in Pediatric Patients During and After Cardiac Surgery," in Pediatrics, vol. 118, No. 3, Sep. 2006.
Peterson et al. "Fiber-optic for in vive measurement of oxygen partial pressure," Analytical Chemistry [online], Jan. 1984 [Retrieved on Nov. 15, 2010], vol. 57, No. 1, pp. 62-67, Retrieved from the Internet: <URL: http://pubs.acs.org>.
Purokoski, Lajunen & Hakkinen, A Potentiometric Study on the Complex Formation of Arsenious Acid, Arsenite Ion, Telluric Acid and Tellurate Ion with Sugar Acids and Disaccharides in Aqueous Solution, Chemical Abstracts, vol. 107, No. 122178n (1987).
Reyes-De-Corcuera, Josi et al.: "Enzyme-electropolymer-based amperometric biosensors: an innovative platform for time-temperature integrators." Journal of Agricultural and Food Chemistry, vol. 53, No. 23, Nov. 1, 2005.
Roy, et al., J. Inorg. Nucl. Chem., 106 (1957).
Seitz, "Chemical Sensors Based on Fiber Optics," Analytical Chemistry, vol. 56, pp. 16a-34a, 1984.
Snyder, et al., "The Preparation of Some Azo Boronic Acids," 70 J. Am. Chem. Soc. 232 (1948).
Stokes, et al.: "An optical oxygen sensor and reaction vessel for high-pressure applications", Limnol. Oceanogr., 44(1),1999,189-195.
Streitwieser, Jr. & Heathcock, Introduction to Organic Chemistry (1976).
Udenfreund, "Fluorescence Assay in Biology and Medicine" (1962) pp. 108-109.
University of Santa Cruz, "Optical Glucose Sensor Holds Promise for Diabetics and Intensive Care Patients", Mar. 18, 2004, in 6 pages.
Van Kempien & Kreuzer, "A Single-Unit Carbon Dioxide Sensing Microelectrode System," Respiration Physiology, (1975), 23, 371-379.
Vermeer, et al., 37 Tetr. Letters 3255 (1970).
Volker, Ludwig et al.: "Continuous Glucose Monitoring with Glucose Sensors: Calibration and Assessment Criteria", Diabetes Technology & Therapeutics, vol. 5, No. 4, Aug. 1, 2003.
Zhujun, Z., et al. (1984). Analytical Chimica Acta 160:305-309.
Zisser, MD, et al. "Excitation: The use of Fluorescence in Glucose Monitoring (Part 11)," Glumetrics, Feb. 13, 2010.
Zochodne D W et al. 1987 Polyneuropathy associated with critical illness: a complication of sepsis and multiple organ failure. Brain, 110: 819-842.
Hunneche, "Antioxidant Activity of a Combinatorial Library of Emulsifier—Antioxidant Bioconjugates," J. Agric. Food Chem. 2008, 56, 9258-9268.
Su et al., "Polyethersulfone Hollow Fiber Membranes for Hemodialysis," Progress in Hemodialysis—From Emergent Biotechnology to Clinical Practice, www.intechopen.com, Nov. 7, 2011. ISBN 978-953-307-377-4.
Japanese Office Action re JP Application No. JP 2010-507711, dated Jun. 19, 2013.

* cited by examiner

EQUILIBRIUM NON-CONSUMING FLUORESCENCE SENSOR FOR REAL TIME INTRAVASCULAR GLUCOSE MEASUREMENT

CROSS-REFERENCE TO RELATED APPLICATIONS

This application claims the priority benefit to U.S. Provisional No. 60/917,307 filed May 10, 2007, the entirety of which is hereby incorporated by reference herein.

BACKGROUND OF THE INVENTION

1. Field of the Invention

Embodiments of the present invention relates to analyte sensors. In particular, the preferred embodiments of the present invention relate to non-consuming intravascular glucose sensors based on fluorescence chemistry.

2. Description of the Related Art

There has been an on-going effort over many years to use fluorescence techniques to measure polyhydroxyl compound (e.g., glucose) concentration in bodily fluids. But despite the effort, no practical system has been developed and commercialized for in vivo monitoring. Several attempts have been made to detect glucose by fluorescence using dyes associated with boronic acid groups. Boronate moieties bind glucose reversibly. When boronic acid functionalized fluorescent dyes bind glucose, the properties of the dye are affected, such that a signal related to the concentration of glucose may be generated and detected. These changes have been used in the past to measure glucose concentration.

Russell (U.S. Pat. Nos. 5,137,833 and 5,512,246) used a boronic acid functionalized dye that bound glucose and generated a signal related to the glucose concentration. James et al. (U.S. Pat. No. 5,503,770) employed a similar principle, but combined a fluorescent dye, an amine quenching functionality, and boronic acid in a single complex. The fluorescence emission from the complex varied with the amount of glucose binding. Van Antwerp et al. (U.S. Pat. Nos. 6,002,954 and 6,011,984) combined features of the previously cited references and also disclosed a device purported to be implantable. A. E. Colvin, Jr. (U.S. Pat. No. 6,304,766) also disclosed optical-based sensing devices for in situ sensing in humans that utilize boronate-functionalized dyes.

Certain measurable parameters using blood or bodily fluid, such as pH and concentrations of $O_2$, $CO_2$, $Na^+$, $K^+$, and polyhydroxyl compounds, like glucose, have been determined in vivo. The ability to do these measurements in vivo is important because it is necessary to make frequent determinations of such analytes when monitoring a patient. Typically, one sensor for each analyte has been placed in a patient's blood vessel(s). If it is desired to measure several analytes, a plurality of sensors is often required, which can cause attendant discomfort to the patient and complexity of the electronic monitoring equipment.

In an effort to solve the design problems posed by the limitation in physical dimension for in vivo monitoring, others have incorporated different dyes into one device to get simultaneous readings of two parameters. For example, Alder et al. (U.S. Pat. No. 5,922,612) disclosed a method for optical determination of pH and ionic strength of an aqueous sample using two different dyes on one sensor. Gray et al. (U.S. Pat. No. 5,176,882) taught the use of a fiber optic device incorporating a hydrophilic polymer with immobilized pH sensitive dye and potassium or calcium sensitive fluorescent dyes to measure the analyte concentration in conjunction with pH. In U.S. Pat. No. 4,785,814, Kane also disclosed the use of two dyes embedded in a composite membrane for the simultaneous measurements of pH and oxygen content in blood. However, incorporation of multiple dyes into a single sensor complicates the manufacture of such sensors.

Besides the foregoing problems associated with separate indwelling sensors for each analyte being monitored, particularly in the intensive care setting, and multiple dye sensors, another problem associated with many dye-based analyte sensors is pH sensitivity. A slight change in pH may modify or attenuate fluorescence emissions, and cause inaccurate readings. This problem is particularly acute for monitoring blood glucose levels in diabetic patients, whose blood pH may fluctuate rapidly. Since accurate blood glucose level measurements are essential for treating these patients, there is a significant need for a glucose sensor that facilitates real-time correction of the pH effect without requiring separate indwelling pH and analyte sensors, or sensors having multiple dyes.

Ratiometric pH determination using fluorescent dye(s) is known. Given a fluorophore that has an acid and base form, the ratio of the emission intensity of the two forms can be used as a measure of the pH that is insensitive to fluorophore concentration . See e.g., U.S. Patent Publication No. 2005/0090014 which describes an HPTS-derived pH sensitive dye (incorporated herein in its entirety by reference); Niu C. G. et al. 2005 *Anal. Bioanal. Chem.* 383(2):349-357, which describes a pH-sensitive dye meso-5,10,15,20-tetra-(4-allyloxyphenyl)porphyrin (TAPP) as an indicator, and a pH-insensitive benzothioxanthene derivative as a reference, for fluorescence ratiometric measurement; Turner N. G. et al. 1998 *J. Investig. Dermatol. Symp. Proc.* August 3(2):110-3, which discloses dual-emission ratiometric imaging using the fluorophore, carboxy seminaphthorhodafluor-1, which displays a pH-dependent shift in its emission spectrum; and Badugu R. et al. 2005 *Talanta* 66:569-574, which describes the use of 6-aminoquinolinium boronic acid dyes that show spectral shifts and intensity changes with pH in a wavelength-ratiometric manner.

However, despite the inventor's recognition of a substantial unmet need for a sensor adapted to provide continuous intravascular monitoring of pH and glucose, wherein the glucose measurement may be corrected for pH effects, no one has disclosed or even suggested using a sensor comprising a single fluorophore that exhibits properties suitable to make a ratiometric pH measurement that is independent of the fluorophore concentration, where the same fluorophore is functionalized to bind glucose and generate a signal the intensity of which is related to the glucose concentration.

SUMMARY OF THE INVENTION

An intravascular sensor is disclosed in accordance with preferred embodiments of the present invention for determining the analyte concentration in blood. The sensor comprises an analyte binding molecule, wherein the analyte binding molecule is associated with a fluorophore; an analyte analog, wherein the analyte analog is associated with an acceptor, wherein the fluorophore is capable of emitting radiation at a wavelength that is absorbed at least in part by the acceptor, wherein the fluorophore is capable of transferring energy to the acceptor via fluorescence resonance energy transfer when the fluorophore is in close proximity to the acceptor; a light source; and a detector.

In some embodiments, the sensor further comprises a hydrogel, wherein the analyte binding molecule and the analyte analog are substantially immobilized in the hydrogel, wherein the hydrogel is permeable to the analyte.

In some embodiments, the light source is a laser.

In some embodiments, the laser is capable of delivering a frequency modulated excitation signal.

In some embodiments, the laser is capable of delivery a pulse of light.

In some embodiments, the sensor further comprises an optical fiber.

In some embodiments, the analyte is glucose.

A method is disclosed in accordance with preferred embodiments of the present invention for determining the glucose concentration in blood. The method comprises providing the sensor as described above; inserting the sensor into a blood vessel; irradiating the fluorophore with an excitation signal; detecting a fluorescence emission from the fluorophore; and determining the concentration of glucose.

In some embodiments, the excitation signal is a pulse of light.

In some embodiments, the method further comprises measuring the decay of the fluorescence emission over time and calculating a fluorescence lifetime.

In some embodiments, the excitation signal is frequency modulated.

In some embodiments, the method further comprises measuring the phase shift between the emission and the excitation signal.

In some embodiments, the method further comprises calculating a fluorescence lifetime.

In some embodiments, the method further comprises measuring a modulation ratio and calculating a fluorescence lifetime.

In one preferred embodiment, an intravascular sensor is disclosed for determining an analyte concentration in blood. The sensor comprises an optical fiber comprising a sensor chemistry portion disposed along a distal region of the optical fiber, wherein the sensor chemistry portion is sized and physiologically compatible with residing in a blood vessel, wherein the sensor chemistry portion is selected from equilibrium fluorescence chemistry or lifetime chemistry.

DETAILED DESCRIPTION OF THE PREFERRED EMBODIMENT

Figure 1:
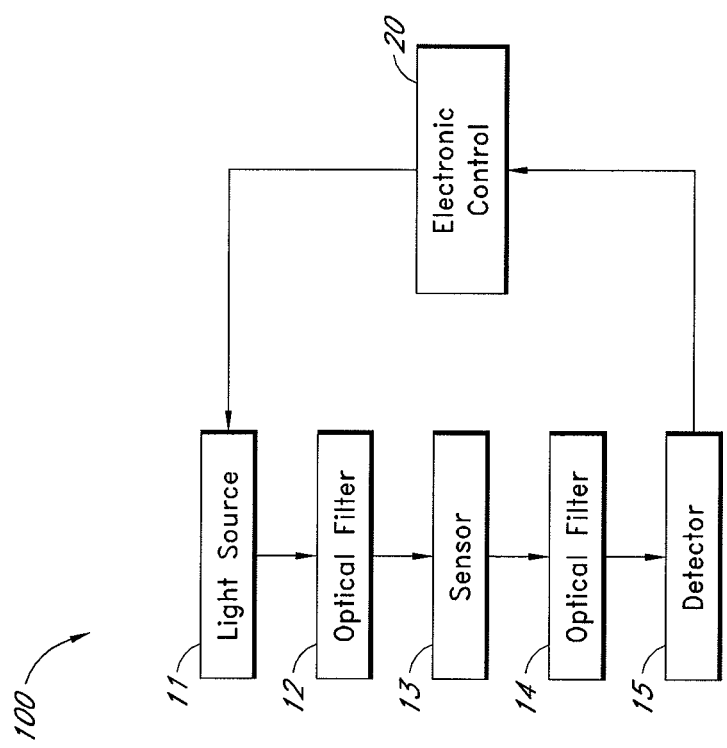
FIG. 1 is a flow chart showing the sensing mechanism of one embodiment of the present invention.

In a preferred embodiment, the present invention is directed to an optical sensor capable of measuring two analytes with a single indicator system. More particularly, the preferred sensor employs a single fluorophore (e.g., a fluorescent dye) to: (1) determine the concentration of a first analyte, e.g., $H^+$ (pH), by a ratiometric method, wherein such determination is independent of the concentration of the fluorophore; and (2) determine the concentration of a second analyte, e.g., a polyhydroxyl compounds (e.g., preferably glucose) by measuring the apparent fluorophore concentration (e.g., emission intensity of the fluorophore upon excitation), wherein the apparent fluorophore concentration is dependent on the concentration of the second analyte. Further, where measurement of the second analyte concentration is dependent on the first analyte concentration (e.g., in optical systems in which glucose measurement varies with pH—a common problem in this field), then in accordance with a preferred embodiment of the present invention, the measured second analyte concentration may be corrected for the contribution of the first analyte concentration. The sensor is preferably stable in aqueous media (e.g., physiological media, blood, interstitial fluid, etc.), and more preferably, the sensor is configured to be inserted into a blood vessel where it can remain indwelling for a period of time. Thus, in accordance with a preferred embodiment of the present invention, an optical sensor configured for intravascular placement is disclosed, which sensor is capable of measuring two analytes (preferably pH and glucose) with a single indicator system and correcting the glucose measurement for any contributions of pH.

Although preferred embodiments of the sensor are directed inter alia to ratiometric pH sensing, other first analyte concentrations may be determined in accordance with the broader scope of the present invention, as long as the indicator system comprises a fluorophore that exists in at least two forms the concentration of which are associated with the concentration of the first analyte and the emission ratio of which is independent of the fluorophore concentration. Likewise, although glucose is used as a second analyte example herein, it is understood that the concentration of other polyhydroxyl-containing organic compounds (carbohydrates, 1,2-diols, 1,3-diols and the like) in a solution may be determined using embodiments of this invention, as long as the indicator system comprises a fluorophore that is operably coupled to a binding moiety that binds the second analyte, wherein the signal intensity of the fluorophore varies with the concentration of second analyte. In some embodiments, the concentration of second analytes may including non-carbohydrates.

Indicator System

The indicator systems used in accordance with preferred embodiments of the present invention comprise a fluorophore operably coupled to an analyte binding moiety, wherein analyte binding causes an apparent optical change in the fluorophore concentration (e.g., emission intensity). It is further desired that the fluorophore has different acid and base forms that exhibit a detectable difference in spectral properties such that ratiometric pH sensing may be enabled. For example, a glucose binding moiety such as 3,3'-oBBV (described in detail below) that is operably coupled to a fluorescent dye such as HPTS-triLysMA (described in detail below) will quench the emission intensity of the fluorescent dye, wherein the extent of quenching is reduced upon glucose binding resulting in an increase in emission intensity related to glucose concentration. In preferred embodiments, the indicator systems comprise a dye having at least two anionic groups and a quencher having at least two boronic acids. In further preferred embodiments, the indicator systems also comprise a means for immobilizing the sensing moieties (e.g., dye-quencher) such that they remain physically close enough to one another to react (quenching). Where in vivo sensing is desired, such immobilizing means are preferably insoluble in an aqueous environment (e.g., intravascular), permeable to the target analytes, and impermeable to the sensing moieties. Typically, the immobilizing means comprises a water-insoluble organic polymer matrix. For example, the HPTS-triLysMA dye and 3,3'-oBBV quencher may be effectively immobilized within a DMAA (N,N-dimethylacrylamide) hydrogel matrix (described in detail below), which allows pH and glucose sensing in vivo.

Some exemplary and preferred fluorophores, analyte binding moieties and immobilizing means are set forth in greater detail below.

Fluorophores

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2$NH—), amide —(C=O)N—, ester —(C=O)—O—, ether. —O—, sulfide —S—, sulfone (—$SO_2$—), phenylene—$C_6H_4$—, urethane—NH(C=O)—O—, urea—NH(C=O)NH—, thiourea —NH(C=S)—NH—, amide —(C=O)NH—, amine—NR— (where R is defined as alkyl having 1 to 6 carbon atoms) and the like, or a combination thereof. In one embodiment, the dye is bonded to a polymer matrix through the sulfonamide functional groups.

In some embodiments, useful dyes include pyranine derivatives (e.g. hydroxypyrene trisulfonamide derivatives and the like), which have the following formula:

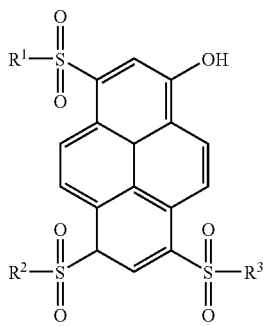

wherein $R^1$, $R^2$, $R^3$ are each —NHR$^4$, $R^4$ is —CH$_2$CH$_2$(—OCH$_2$CH$_2$—)$_n$X$^1$; wherein X$^1$ is —OH, —OCH$_3$COOH, —CONH$_2$, —SO$_3$H, —NH$_2$, or OMe; and n is between about 70 and 10,000. In one embodiment, the dyes may be bonded to a polymer through the sulfonamide functional groups. In other embodiments, the dye may be one of the polymeric derivatives of hydroxypyrene trisulfonic acid.

In some embodiments, the fluorescent dye may be 8-hydroxypyrene-1,3,6-trisulfonate (HPTS). The counterions can be H$^+$ or any other cation. HPTS exhibits two excitation wavelengths at around 450 nm and around 405 nm, which correspond to the absorption wavelengths of the acid and its conjugate base. The shift in excitation wavelength is due to the pH-dependent ionization of the hydroxyl group on HPTS. As the pH increases, HPTS shows an increase in absorbance at about 450 nm, and a decrease in absorbance below about 420 nm. The pH-dependent shift in the absorption maximum enables dual-excitation ratiometric detection in the physiological range. This dye has a molecular weight of less than 500 daltons, so it will not stay within the polymer matrix, but it can be used with an anion exclusion membrane.

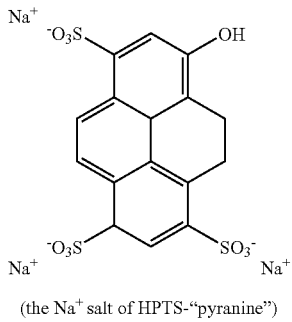

(the Na$^+$ salt of HPTS-"pyranine")

In another embodiment, the fluorescent dye may be polymers of 8-acetoxy-pyrene-1,3,6- N, N',N"-tris- (methacrylpropyl amidosulfonamide) (acetoxy- HPTS-MA):

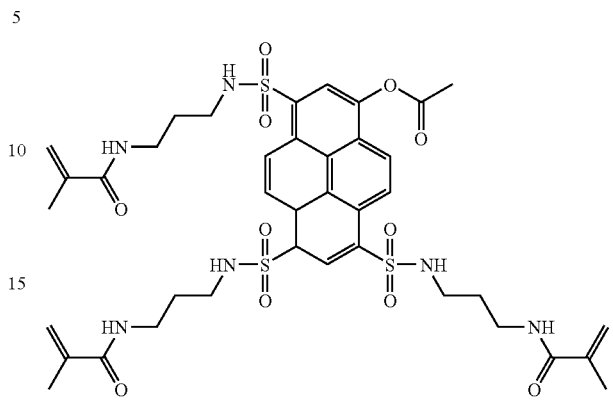

It is noted that dyes such as acetoxy-HPTS-MA (above) having no anionic groups, may not give very strong glucose response when operably coupled to a viologen quencher, particularly a viologen quencher having only a single boronic acid moiety.

In another embodiment, the fluorescent dye may be 8-hydroxy-pyrene-1,3,6-N,N',N"-tris-(carboxypropylsulfonamide) (HPTS-CO$_2$):

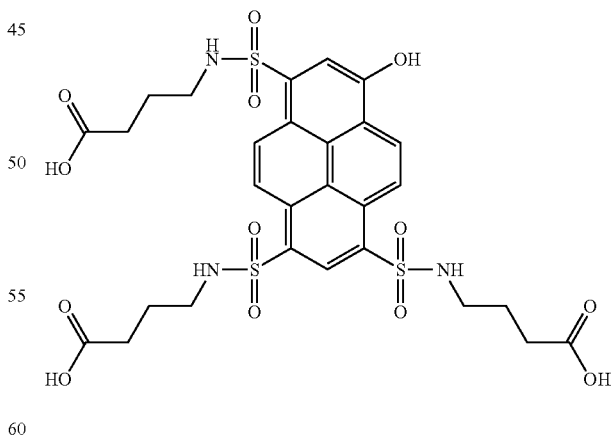

In another embodiment, the fluorescent dye may be 8-hydroxy-pyrene-1,3,6-N,N',N"-tris-(methoxypolyethoxyethyl (~125) sulfonamide) (HPTS-PEG):

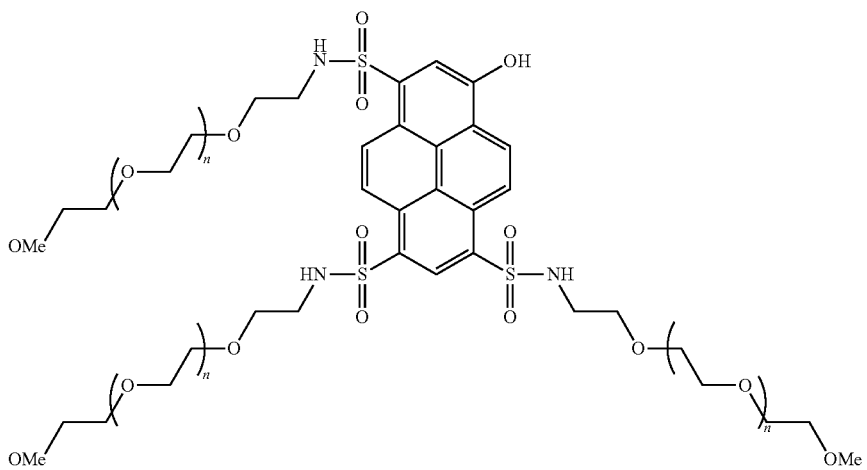

It is noted that dyes such as HPTS-PEG (above) having no anionic groups, may not provide a very strong glucose response when operably coupled to a viologen quencher, particularly a viologen quencher having only a single boronic acid moiety.

Representative dyes as discrete compounds are the tris adducts formed by reacting 8-acetoxypyrene-1,3,6-trisulfonylchloride (HPTS-Cl) with an amino acid, such as amino butyric acid. Hydroxypyrene trisulfonamide dyes bonded to a polymer and bearing one or more anionic groups are most preferred, such as copolymers of 8-hydroxypyrene-1-N-(methacrylamidopropylsulfonamido)-N',N''-3,6-bis(carboxypropylsulfonamide) HPTS-CO$_2$-MA with HEMA, PEGMA, and the like.

In another embodiment, the fluorescent dye may be HPTS-TriCys-MA:

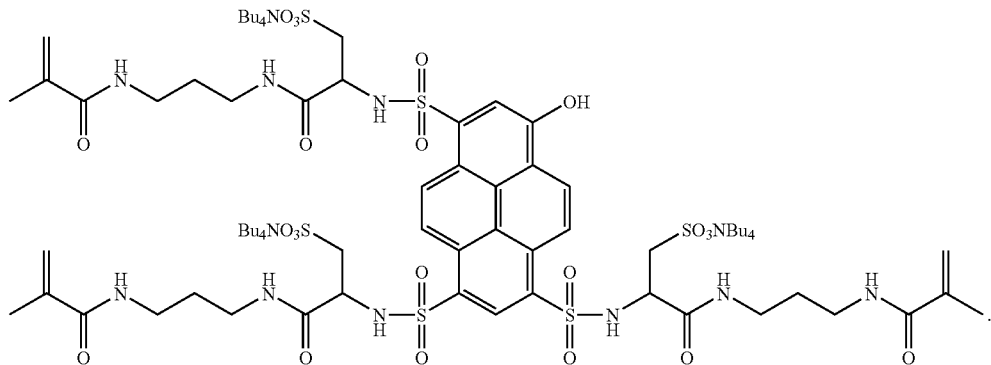

This dye may be used with a quencher comprising boronic acid, such as 3,3'-oBBV.

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counterions besides $NBu_4^+$ may be used, including positively charged metals, e.g., $Na^+$. In other variations, the sulfonic acid groups may be replaced with e.g., phosphoric, carboxylic, etc. functional groups.

Another suitable dye is HPTS-LysMA, which is pictured below as follows:

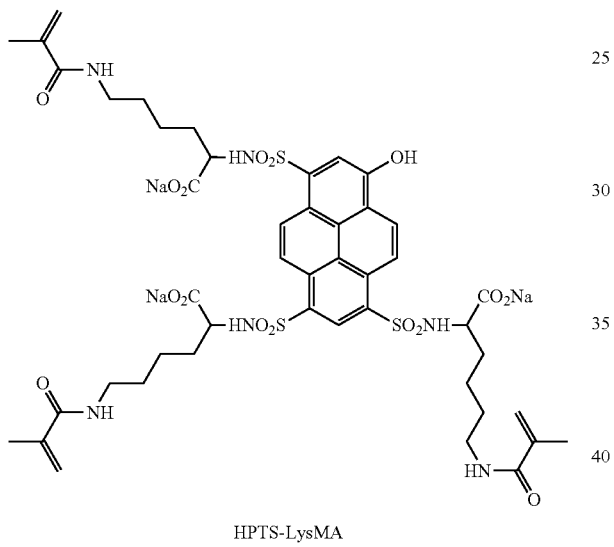

HPTS-LysMA

Other examples include soluble copolymers of 8-acetoxypyrene-1,3,6-N, N',N'''-tris(methacrylamidopropylsulfonamide) with HEMA, PEGMA, or other hydrophilic comonomers. The phenolic substituent in the dye is protected during polymerization by a blocking group that can be removed by hydrolysis after completion of polymerization. Such suitable blocking groups, as for example, acetoxy, trifluoroacetoxy, and the like, are well known in the art.

Fluorescent dyes, including HPTS and its derivatives are known and many have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 11/296,898 and 60/833,081; each of which is incorporated herein in its entirety by reference thereto.

The SNARF and SNAFL dyes from Molecular Probes may also be useful fluorophores in accordance with aspects of the present invention. The structures of SNARF-1 and SNAFL-1 are shown below.

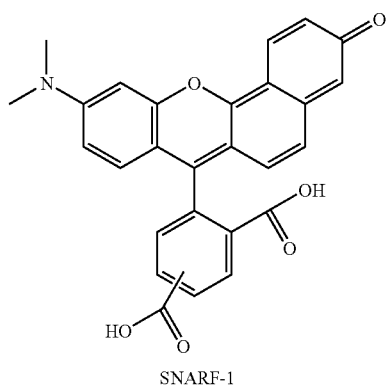

SNARF-1

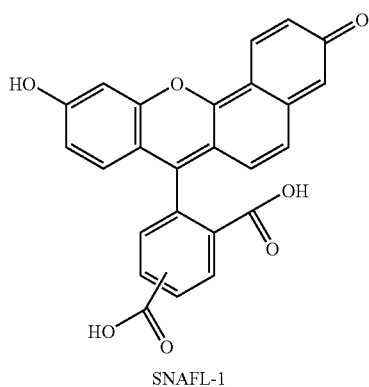

SNAFL-1

Additionally, a set of isomeric water-soluble fluorescent probes based on both the 6-aminoquinolinium and boronic acid moieties which show spectral shifts and intensity changes with pH, in a wavelength-ratiometric and calorimetric manner may be useful in accordance with some embodiments of the present invention (See e.g., Badugu, R. et al. 2005 Talanta 65 (3):762-768; and Badugu, R. et al. 2005 Bioorg. Med. Chem. 13 (1):113-119); incorporated herein in its entirety by reference.

Another example of a fluorescence dye that may be pH and saccharide sensitive is tetrakis(4-sulfophenyl)porphine (TSPP)-shown below. TSPP may not work optimally in blood, where the porphyrin ring may react with certain metal ions, like ferric, and become non-fluorescent.

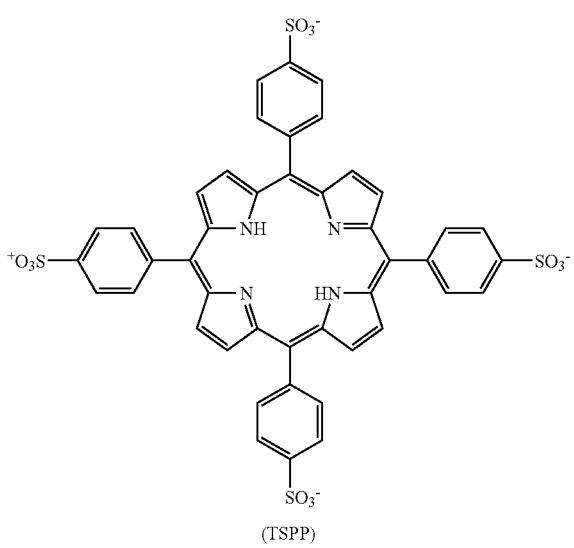
(TSPP)

Additional examples of pH sensitive fluorescent indicators that may be useful for simultaneous determination of pH and glucose in the sensor of the present invention are described in US 2005/0233465 and US 2005/0090014; each of which is incorporated herein by reference in its entirety.

Analyte Binding Moieties—Quenchers

In accordance with broad aspects of the present invention, the analyte binding moiety provides the at least dual functionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

In one example, the moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N'bis-(benzyl) bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorphore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

Bis-onium salts in the embodiments of this invention are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this invention. In one embodiment, the quencher may be one of the bis-onium salts derived from 3,3'-dipyridyl, 4,4'-dipyridyl and 4,7-phenanthroline.

In some embodiments, the viologen-boronic acid adduct may be a discrete compound having a molecular weight of about 400 daltons or greater. In other embodiments, it may also be a pendant group or a chain unit of a water-soluble or water-dispersible polymer with a molecular weight greater than about 10,000 daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the viologen-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix $M^2$, which can be represented by the structure $M^2$-$L^2$-Q. $L^2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

For the polymeric quencher precursors, multiple options are available for attaching the boronic acid moiety and a reactive group which may be a polymerizable group or a coupling group to two different nitrogens in the heteroaromatic centrally located group. These are:

a) a reactive group on a first aromatic moiety is attached to one nitrogen and a second aromatic group containing at least one —B(OH)2 group is attached to the second nitrogen;

b) one or more boronic acid groups are attached to a first aromatic moiety which is attached to one nitrogen and one boronic acid and a reactive group are attached to a second aromatic group which second aromatic group is attached to the second nitrogen;

c) one boronic acid group and a reactive group are attached to a first aromatic moiety which first aromatic group is attached to one nitrogen, and a boronic acid group and a reactive group are attached to a second aromatic moiety which is attached to the second nitrogen; and d) one boronic acid is attached to each nitrogen and a reactive group is attached to the heteroaromatic ring.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho- meta or para-positions.

In some embodiments, the boronic acid substituted viologen as a discrete compound useful for in vitro sensing may be represented by one of the following formulas:

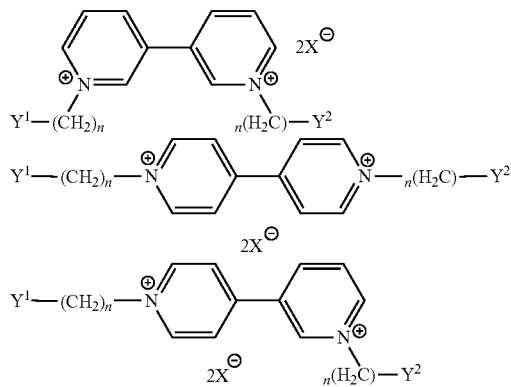

where n=1-3, X is halogen, and $Y^1$ and $Y^2$ are independently selected from phenyl boronic acid (o- m- or p-isomers) and naphthyl boronic acid. In other embodiments, the quencher may comprise a boronic acid group as a substituent on the heterocyclic ring of a viologen.

A specific example used with TSPP is m-BBV:

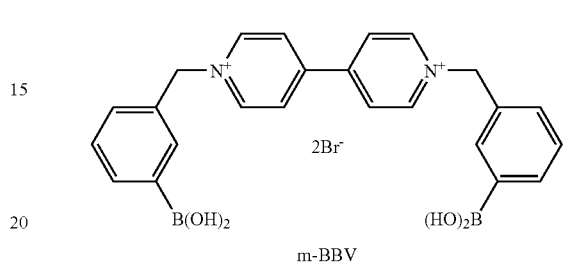

m-BBV

The quencher precursors suitable for making sensors may be selected from the following:

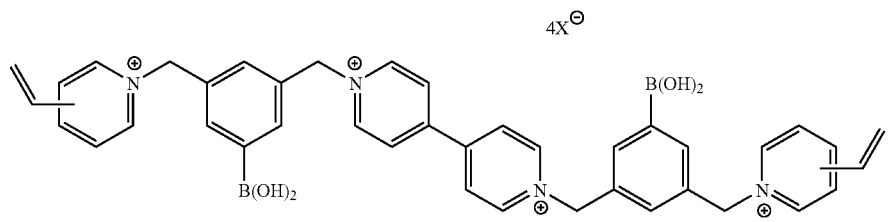

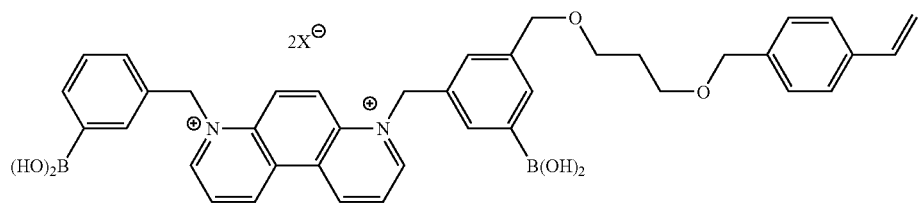

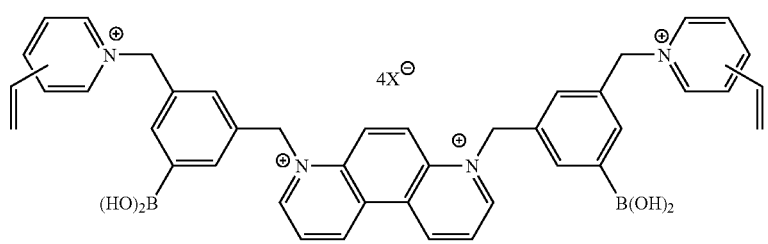

-continued
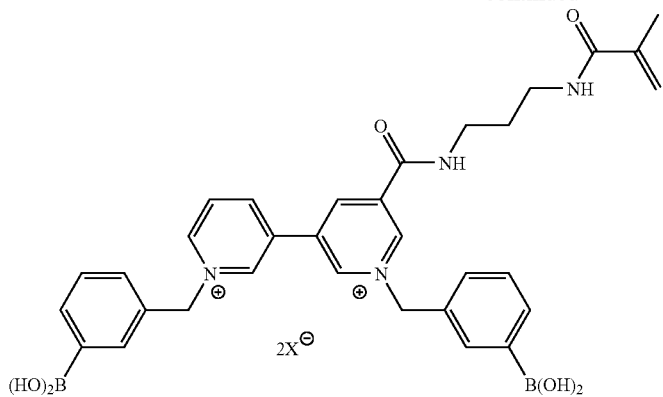
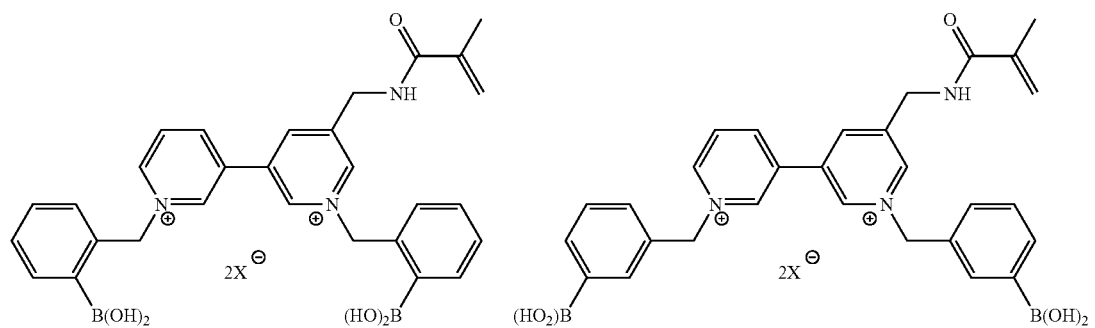
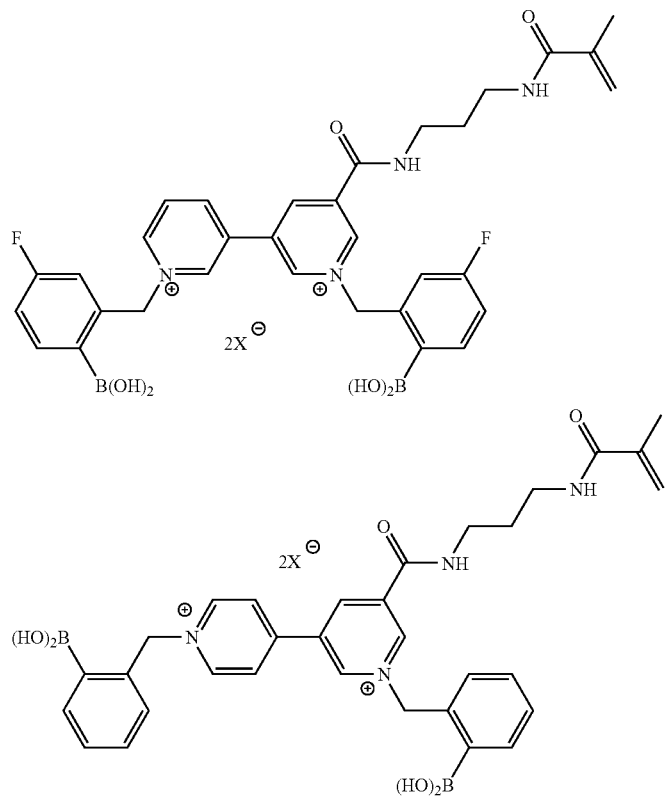

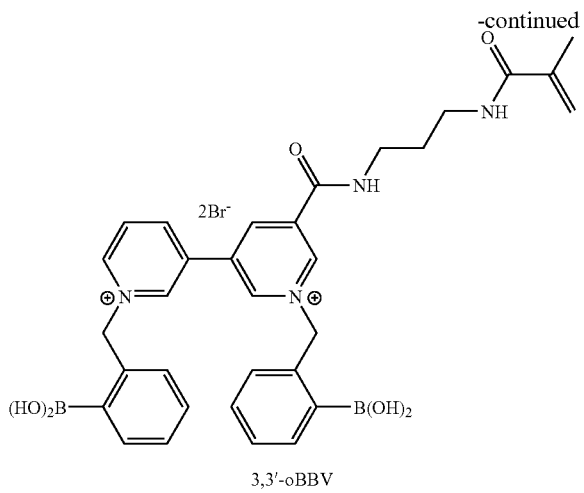

3,3'-oBBV

The quencher precursor 3,3'-oBBV may be used with HPTS-LysMA or HPTS-CysMA to make hydrogels in accordance with preferred aspects of the invention.

Preferred quenchers are prepared from precursors comprising viologens derived from 3,3'-dipyridyl substituted on the nitrogens with benzylboronic acid groups and at other positions on the dipyridyl rings with a polymerizable group or a coupling group. Representative viologens include:

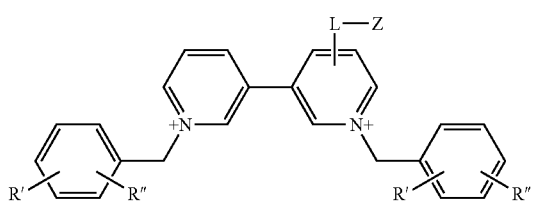

where L is L1 or L2 and is a linking group
Z is a reactive group; and
R' is —B(OH)$_2$ in the ortho- meta- or para-positions on the benzyl ring and R" is H—; or optionally R" is a coupling group as is defined herein or a substituent specifically used to modify the acidity of the boronic acid such as fluoro- or methoxy- L is a divalent moiety that covalently connects the sensing moiety to a reactive group that is used to bind the viologen to a polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$-, urethane —NH(C═O)—O—, urea —NH(C═O)NH—, thiourea —NH(C═S)—NH—, amide —(C═O)NH—, amine —NR— (where R is defined as alkyl having 1 to 6 carbon atoms) and the like.

Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$.

Boronic acid substituted polyviologens are another class of preferred quenchers. The term polyviologen includes: a discrete compound comprised of two or more viologens covalently bonded together by a linking group, a polymer comprised of viologen repeat units in the chain, a polymer with viologen groups pendant to the chain, a dendrimer comprised of viologen units, preferably including viologen terminal groups, an oligomer comprised of viologen units, preferably including viologen endgroups, and combinations thereof. Polymers in which mono-viologen groups form a minor component are not included. The preferred quenchers are water soluble or dispersible polymers, or crosslinked, hydrophilic polymers or hydrogels sufficiently permeable to glucose to function as part of a sensor. Alternatively the polyviologen boronic acid may be directly bonded to an inert substrate.

A polyviologen quencher as a polymer comprised of viologen repeat units has the formula:

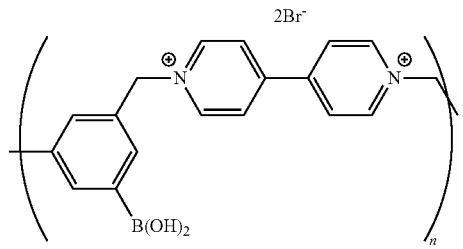

In another embodiment, the polyviologen boronic acid adducts are formed by covalently linking two or more viologen/boronic acid intermediates. The bridging group is typically a small divalent radical bonded to one nitrogen in each viologen, or to a carbon in the aromatic ring of each viologen, or one bond may be to a ring carbon in one viologen and to a nitrogen in the other. Two or more boronic acid groups are attached to the polyviologen. Optionally, the polyviologen boronic acid adduct is substituted with a polymerizable group or coupling group attached directly to the viologen or to the bridging group. Preferably the polyviologen moiety includes only one such group. Preferably, the bridging group is selected to enhance cooperative binding of the boronic acids to glucose.

The coupling moiety is a linking group as defined previously with the proviso that the linking group is optionally further substituted with a boronic acid, a polymerizable group, an additional coupling group, or is a segment in a polymer chain in which the viologen is a chain unit, a pendant group, or any combination thereof.

Immobilizing Means

In some embodiments, for use in vitro not involving a moving stream, the sensing components are used as individual (discrete) components. The dye and quencher are mixed together in liquid solution, analyte is added, the change in fluorescence intensity is measured, and the components are discarded. Polymeric matrices that can be used to trap the sensing components to prevent leaching need not be present. Optionally, the sensing components are immobilized which allows their use to measure analytes in a moving stream.

For in vivo applications, the sensor is used in a moving stream of physiological fluid which contains one or more polyhydroxyl organic compounds or is implanted in tissue such as muscle which contains said compounds. Therefore, it is preferred that none of the sensing moieties escape from the sensor assembly. Thus, for use in vivo, the sensing components are preferably part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N',N''-tris(methacrylamidopropylsulfonamide), the quencher moiety is derived from an ethylenically unsaturated viologen such as 4-N-(benzyl-3-boronic acid)-4'-N'-(benzyl-4ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-

N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and polymerizing the mixture. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorescent dye and quencher moieties while at the same time allowing contact with the analytes (e.g., polyhydroxyl compounds, $H^+$ and $OH^-$), and binding of the polyhydroxyl compounds to the boronic acid. Therefore, the matrix is insoluble in the medium and in close association with it by establishing a high surface area interface between matrix and analyte solution. The matrix also does not interfere with transport of the analyte to the binding sites so that equilibrium can be established between the two phases. In one embodiment, an ultra-thin film or microporous support matrix may be used. In another embodiment, the matrix that is swellable in the analyte solution (e.g. a hydrogel matrix) can be used for aqueous systems. In some embodiments, the sensing polymers are bonded to a surface such as the surface of a light conduit, or impregnated in a microporous membrane. Techniques for preparing ultra-thin films, microporous polymers, microporous sol-gels, and hydrogels have been established in the prior art.

In one preferred embodiment, the boronic acid substituted viologen may be covalently bonded to a fluorescent dye. The adduct may be a polymerizable compound or a unit in a polymer. One such adduct for example may be prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxy-pyrene-1,3,6-trisulfonyl chloride in a 1:1 mole ratio followed by reaction with excess PEG diamine to obtain a prepolymer mixture. An acid acceptor is included in both steps to scavange the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups may be reacted with methacrylol chloride. After purification, the dye/viologen monomer may be copolymerized with HEMA and PEGDMA to obtain a hydrogel.

Ratiometric pH Sensing

Ratiometric pH sensing is known. See e.g., US Pat. Publication Nos. 2006/0105174; 2005/0090014; incorporated herein in their entirety by reference. Given an indicator system comprising a fluorophore (e.g., a fluorescent indicator dye) that exists in two forms (an acid form and a base form) the ratio of the emission intensity at the two wavelengths can be used to measure pH independent of the fluorophore concentration. The fluorescent indicator dyes suitable for ratiometric pH sensing may be: (1) dyes that exhibit dual excitation wavelengths (corresponding to acid and conjugate base forms) and single emission wavelengths (e.g., HPTS dyes); (2) single excitation wavelengths and dual emission wavelengths (acid and base forms); or (3) dual excitation - dual emission dyes. Some dyes, such as the SNARF or SNAFL dyes may have both dual-emission and dual-excitation properties. However a dual-dual dye, e.g., SNARF can be used as a single-dual or a dual-single.

Dual emission fiber-optic sensors based on seminapthofluorescein and carboxynaphthofluorescein have been described that rapidly and reliably correlate intensity ratios to pH. See e.g., respectively, Xu, Z., A. Rollins, et al. (1998) "A novel fiber-optic pH sensor incorporating carboxy SNAFL-2 and fluorescent wavelength-ratiometric detection" Journal of Biomedical Materials Research 39: 9-15, and Song, A., S. Parus, et al. (1997) "High-performance fiber-optic pH microsensors for practical physiological measurements using a dual-emission sensitive dye" Analytical Chemistry 69: 863-867. The extensive photobleaching observed for these dyes may be accounted for by the ratiometric approach, but it would still limit the useful lifetime of the sensor.

The fluorescent dye 8-hydroxy-1,3,6-pyrene trisulphonic acid trisodium salt (HPTS) consists of a pyrene core with three sulfonic acid groups and a hydroxyl group that imparts pH sensitivity around a pKa of approximately 7.3 (Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314

(2): 119-124); Wolfbeis et al. also have several patents on immobilized HPTS. Yafuso and Hui describe another immobilized fluorescent dye pH sensor in U.S. Pat. No. 4,886,338; incorporated herein in its entirety by reference thereto. HPTS exhibits two excitation wavelengths, one at 405 nm and one at 457 nm, that correspond to the acid and its conjugate base (Agayn, V. I. and Dr. R. Walt (1993). "Fiber-optic sensor for continuous monitoring of fermentation pH." Biotechnology 72(6):6-9). The subsequent pH-dependent shift in excitation maximum about the pKa of 7.3 enables dual-excitation/single emission ratiometric detection in the physiological range. This, together with a low toxicity (Lutty, G. A. (1978). "The acute intravenous toxicity of stains, dyes, and other fluorescent substances." Toxical Pharmacol. 44: 225-229) and insensitivity to oxygen concentration (Zhujun, Z. and W. R. Seitz (1984). "A fluorescence sensor for quantifying pH in the range from 6.5 to 8.5." Analytical Chimica Acta 160: 47-55), makes HPTS a suitable probe for physiological and bioprocess pH measurements.

The presence of the three strongly anionic sulphonic acid groups allows for HPTS to be immobilized by ionic binding to cationic supports. To date, covalent attachment of HPTS has been via sulfonamide coupling (U.S. Pat. No. 4,798,738). While effective in immobilizing the dye and preserving pH sensitivity, polymer substrates are limited to those that contain primary amines. In addition, amine groups which remain on the substrate after coupling will affect the local pH inside the polymer matrix. The dye has been covalently attached to controlled pore glass (Offenbacher, H., O. S. Wolfbeis, et al. (1986). "Fluorescence optical sensors for continuous determination of near-neutral pH values." Sensor Actuator 9: 73-84) and aminoethyl cellulose (Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170) in the development of fluorescence-based pH sensors that operate in neutral and acidic environments, as well as an intravascular blood gas monitoring system where it was used for both pH and $pCO_2$ detection (Gehrich, J. L., D. W. Lubbers, et al. (1986). "Optical fluorescence and its application to an intravascular blood gas monitoring system." IEE TBio-med Eng BME-33: 117-132). Fiber-optic pH sensors have been described with HPTS bound to an anion exchange membrane (Zhujun, Z. and W. R. Seitz (1984)) or resin (Zhang, S., S. Tanaka, et al. (1995). "Fibre-optical sensor based on fluorescent indicator for monitoring physiological pH values." Med Biol Eng Comput 33: 152-156) and fixed to the tip of the optical fiber.

For example U.S. Pat. No. 5,114,676 (incorporated by reference herein in its entirety) provides a pH sensor with a fluorescent indicator which may be covalently attached to a particle or to a microcrystalline cellulose fiber. The sensor comprises an optically transparent substrate, a thermoplastic layer and a hydrogel. Part of the particle with the indicator attached thereto is imbedded in a thermoplastic layer that is coated on the substrate and mechanically adhered using heat and pressure. The majority of the particle/indicator is imbedded within a hydrogel layer that is applied over the thermoplastic layer. The pH sensor is applied to the tip of an optical waveguide.

Furthermore, with the recent availability of low cost UV LEDs, the dye can be measured with relatively inexpensive instrumentation that combines UV and blue LEDs and a photodiode module. Such a setup has been described (Kostov, Y., P. Harms, et al. (2001). "Low-cost microbioreactor for high-throughput bioprocessing." Biotechnol Bioeng 72: 346-352) to detect the pH of a high throughput microbioreactor system via HPTS directly dissolved in the fermentation media.

In one embodiment of the present invention, the preferred sensing device comprises at least one light source, a detector, and a sensor comprising a fluorescent reporter dye system. In one embodiment, the fluorescent reporter dye system comprises a fluorescent dye operably coupled to an analyte-binding quencher. The dye may be covalently bound to the quencher or merely associated with the quencher. The dye and quencher are preferably operably coupled, which means that in operation, the quencher is in close enough proximity to the dye to interact with and modulate its fluorescence. In one embodiment, the dye and quencher may be constrained together within an analyte-permeable hydrogel or other polymeric matrix. When excited by light of appropriate wavelength, the fluorescent dye emits light (e.g., fluoresces). The intensity of the light is dependent on the extent of quenching which varies with the amount of analyte binding. In other embodiments, the fluorescent dye and the quencher may be covalently attached to hydrogel or other polymeric matrix, instead of to one another.

In one embodiment, a separate pH indicator dye is combined with a different dye that is functionalized with an analyte-binding moiety, such that the two dye system are immobilized together (e.g., in a hydrogel) in the sensor.

Some fluorescent pH indicator molecules absorb light at a particular wavelength and emit light at a second, longer wavelength. Their pH indicating function typically involves protonation and deprotonation. This means that these fluorescent pH indicators include a hydrogen atom (proton, $H^+$) which forms part of the molecule (is bound to the molecule) in one pH range, but within another pH range the proton is dissociated from the molecule. When the proton is disassociated from the molecule, the molecule takes on a negative charge, which is balanced by a positively-charged ion (e.g., $Na^+$) in solution with the indicator. This arrangement is illustrated by Equation 1. $R\text{—}H \leftrightarrows R^- + H^+$ Where R represents a fluorescent molecule, it generally will exhibit fluorescence at a different wavelength (will be visible as a very different color) based upon whether it is in the R—H form or in the $R^-$ form. For most molecules represented by R, this change will occur generally quite abruptly within a very narrow pH range, allowing R to serve as a very simple and reliable pH indicator. When placed in solution, it will exhibit one very distinct color (a color associated with its R—H form), and another very distinct color associated with its $R^-$.

For example, 8-Hydroxyl-1,3,6-pyrenetrisulphonate (HPTS) has been considered one of the best potential indicators for pH determination because of its excellent photostability, high quantum yield, dual excitation, large Stokes' shift and long fluorescence emission. A desirable feature of this indicator is that the acidic (associated HPTS form) and basic (dissociated $PTS^-$) forms have different excitation wavelengths at 406 and 460 nm, with an isosbestic point at 418 nm, but exhibit a similar fluorescence emission maximum at 515 nm. The dual excitation and single emission make HPTS suitable for ratiometric detection of pH. The fluorescence intensity at 406 nm for the acid form decreases but the intensity at 460 nm for the base form increases as the pH is raised accompanying the conversion of the acidic into basic forms of the dye.

Due to the hydroxyl (—OH) group on dyes such as HPTS and its derivatives, these dyes are sensitive to the pH changes in the environment. The pH-dependent ionization of the hydroxyl group causes these pyranine derivatives to have a pH-dependent absorption spectra with different absorption maxima in its acidic form and basic form. The first absorption maximum is the first excitation wavelength and the second absorption maximum is the second excitation wavelength. The amounts of light absorbed by the fluorescent dye at the first excitation wavelength and the second excitation wavelength depend on or relate to the pH of the medium the fluorescent dye is in contact with. The amount of light emitted by the dye (e.g., the fluorescent emission) at the emission wavelength depends on the amount of light absorption when the dye is irradiated at the excitation wavelength. Since the absorption is affected by the pH of the medium, the fluorescent emission is also affected by the pH. This provides the basis for the pH determination while being able to measure the polyhydroxyl compound concentration.

In one preferred embodiment of the present invention, ratiometric pH sensing is accomplished using an optical sensor comprising at least one excitation light source operably coupled to the proximal end region of an optical fiber, wherein the fiber has disposed along its distal end region within the light path of the fiber, an indicator system configured to generate a detectable emission signal in response to the excitation light. Preferred embodiments of the sensor further comprise optical means for sending the emission signal to a detector. Such optical means are well known in the art, and may involve e.g., a mirror to return light, filters, lens, beam splitters, and optical fiber bundles and split configurations.

In preferred embodiments, the indicator system comprises a fluorophore that exhibits at least two different forms and a pH-dependent shift between these different forms, wherein this shift can be detected as a change in the emission intensity at a single wavelength or at two different wavelengths. For example, one indicator system for ratiometric pH sensing comprises an fluorescent dye (e.g., HPTS) that absorbs light at two different wavelength maxima's ($\lambda_{acid}$ and $\lambda_{base}$) depending on whether the dye is in its acid or base forms, and it emits light at a single longer emission wavelength. More particularly, as pH is increased, HPTS shows an increase in absorbance corresponding to the $\lambda_{base}$ and a decrease in absorbance corresponding to the $\lambda_{acid}$. These changes are due to the pH-dependent ionization of the hydroxyl group. The emission spectrum for HPTS is independent of pH, with a peak emission wavelength of about 511 nm, but the intensity of the emitted light depends on the amount of light absorbed (which varies with pH and the excitation wavelength). So for example, if one excites HPTS at a given pH with light of a first wavelength (e.g., $\lambda_{acid}$), one can measure the emission intensity at the single emission wavelength; the intensity will depend on the form of the dye (i.e., degree of ionization—which depends on the pH). One can also excite at a second wavelength (e.g., $\lambda_{base}$) and measure the emission intensity at the same given pH. The ratio of the emission intensities relates to the pH and is independent on the amount of the dye as well as certain optical artifacts in the system. It is noted that any excitation wavelengths may be used for the ratiometric sensing, but the $\lambda_{acid}$ and $\lambda_{base}$ are preferred in accordance with one embodiment of the invention. The wavelength at which the absorption is the same for the acid and base forms of the dye is called the isobestic point-excitation at this wavelength ($I_{iso}$) may also be used in ratiometric sensing in accordance with other preferred variations to the invention. When a ratio of emission intensities (e.g., $I_{base}/I_{iso}$ or $I_{base}/I_{acid}$) is plotted against pH, a standard or calibration curve is generated (See e.g., FIGS. 3, 5 and 9). The ratiometric method is similar regardless of whether the dye used is a dual exciter-single emitter (like HPTS), or a single exciter—dual emitter, or a dual exciter—dual emitter, as long as the dye undergoes a pH sensitive shift in form that yields a detectable change in spectral property.

Optical Glucose Sensing

Indicator systems comprising fluorescent dyes, including HPTS and its derivatives, have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 11/296,898 and 60/833,081; each of which is incorporated herein in its entirety by reference thereto. In particular, details related to some preferred fluorescent dyes, quenchers/analyte binding moieties, and methods for optically determining polyhydroxyl compound concentrations are disclosed in U.S. Pat. Nos. 6,653,141 and 6,627,177, and U.S. patent application Ser. Nos. 11/296,898 and 60/833,081.

Device for Intravascular Determination of pH and Glucose

In one embodiment, the method and sensor monitor the pH of the media and the concentration of analyte in vitro. In another embodiment, the method and sensor monitor pH and analyte concentration in vivo. In another embodiment, the measured pH value can also be used to more correctly determine glucose concentration in vitro or in vivo. Specifically, the simultaneous measurement of the pH value and the glucose concentration would enable real time correction of the signal of glucose response. Although it will be appreciated that the device in accordance with some embodiments comprise a sensor that may be used only to determine pH or analyte (correction of which for pH may be done by conventional two sensor technologies or by testing the blood pH in vitro).

One embodiment provides a device for determining pH and the concentration of a polyhydroxyl compound simultaneously, comprising a sensor comprising a fluorescent dye operably coupled to a quencher; means for delivering one or more excitation wavelengths to said sensor; and means for detecting fluorescence emission from said sensor.

Another embodiment provides a device for determining the pH and the polyhydroxyl compound concentration in a physiological fluid, comprising a water-insoluble polymer matrix, wherein said polymer matrix is permeable to polyhydroxyl compound; a fluorescent dye associated with said polymer matrix, wherein the fluorescent dye is configured to absorb light at a first excitation wavelength and a second excitation wavelength, and to emit light at an emission wavelength; a quencher comprising an aromatic boronic acid substituted viologen, adapted to reversibly bind an amount of polyhydroxyl compound dependent on the polyhydroxyl compound concentration, wherein said quencher is associated with said polymer matrix and operably coupled to the fluorescent dye, and wherein the quencher is configured to reduce the light intensity emitted by said fluorescent dye related to the amount of bound polyhydroxyl compound; at least one excitation light source; and an emission light detector.

In one aspect, the present invention comprises a class of fluorescence quenching compounds that are responsive to the presence of polyhydroxyl compounds such as glucose in aqueous media at or near physiological pH. In other words, the quenching efficiency is controlled by the concentration of these compounds in the medium. Preferred quenchers comprise a viologen substituted with at least one boronic acid group wherein the adduct is immobilized in or covalently bonded to a polymer. The quencher, dye and polymer may also be covalently bonded to each other. In another aspect, the present invention comprises a class of fluorescent dyes which are susceptible to quenching by the viologen/boronic acid adduct.

The fluorescent dye and quencher are operably coupled to each other for polyhodoxyl compound sensing. The dye and quencher may be linked through a polymer backbone in some embodiments. In other embodiments, the dye and quencher could be in close proximity to each other for the quenching of the fluorescent dye to occur, thereby reducing the fluorescent emission of the dye. When polyhydroxyl compound (e.g., glucose) binds to the boronic acid to form boronate ester, the boronate ester interacts with the viologen and alters its quenching efficacy according to the extent of polyhydroxyl compound binding. As a result, the intensity of fluorescent emission increases as more polyhydroxyl compounds are bonded to the quenchers.

In one preferred embodiment, the device comprises an optical fiber comprising a cavity disposed therein and having immobilized within the cavity an indicator system as described above (e.g., a fluorophore operably coupled to a glucose binding moiety/quencher and an immobilizing polymeric matrix). The device further comprises a light source and a detector.

Methods for Simultaneous Determination of pH and Glucose

One embodiment provides a method for determining the pH and the polyhydroxyl compound concentration with one fluorescent dye, comprising providing a sensor comprising a fluorescent dye operably coupled to a quencher; contacting said sensor with a sample; irradiating said sensor at the first excitation wavelength; detecting a first fluorescence emission of said sensor at an emission wavelength; irradiating said sensor at the second excitation wavelength; measuring a second fluorescence emission of said sensor at said emission wavelength; comparing the ratio of the first and second emissions with a pH calibration curve to determine the pH of the sample; correlating the emission quenching with a standard curve at the known pH to determine the polyhydroxyl compound concentration in said sample. Of course other algorithms are known for ratiometric pH sensing and may be used in accordance with embodiments of the present invention. A controller, such as a computer or dedicated device, may be used in some embodiments to control the operations, including application of the excitation light, monitoring of detector signals, determining ratios, correlating ratios with calibration curves, correlating glucose signals with standard curves, correcting for pH changes, running routine sensor calibration operations, prompting operator actions, integrating user data input (e.g., finger stick glucose measurements) as programmed to maintain accuracy, etc.

With respect to FIG. 1, a sensing device 100 in accordance with one embodiment of the present invention comprises at least one light source 11 (e.g., an excitation light source), a detector 15 (e.g., an emission light detector), and a sensor 13 comprising a fluorescent dye operably coupled to a quencher and an optional polymer matrix. In some embodiments, the light source 11 may be adapted to selectively deliver two or more different wavelength for the excitations of fluorescent dyes. This type of light source may be a tunable light source. In other embodiments, one or more light sources may be used in conjunction with an optical filter 12 for attenuating the wavelengths. In other embodiments, more than one light source 11 may be used to deliver different excitation wavelengths. Such light source is also a means for delivering a first and a second excitation wavelengths to the sensor.

The sensor 13 comprises a fluorescent dye that is sensitive to both the pH and the polyhydroxyl compound (e.g., sugar or glucose) concentration of the medium when the dye is operably coupled to a quencher. Such fluorescent dye exhibits a shift in excitation wavelength maximum with a corresponding shift in pH of the local environment of the fluorescent dye. As the pH of the local environment changes, the absorption at a first excitation wavelength may increase, while the absorption at a second excitation wavelength decreases, or vice versa. The change in absorption at a selected wavelength can affect the level of fluorescence emission, therefore ultimately permitting pH detection. The pH detection is independent of the concentration of the polyhydroxyl compound in the environment. A suitable fluorescent dye is also susceptible to quenching by molecules such as viologens. When the fluorescent dye is operably coupled to a quencher (e.g., a viologen), the fluorescence emission is attenuated. The quencher may have an aromatic boronic acid moiety that is capable of providing glucose recognition. The boronic acid reacts reversibly with glucose in aqueous media to form boronate ester, and the extent of such reaction is related to the glucose concentration in the medium. As more glucose is available to react with the quencher, the quencher's ability to accept electron from the dye decreases. As a result, the attenuation of fluorescence emission by the quencher is dependent on the concentration of the polyhydroxyl compound (e.g., glucose) to be detected.

A detector 15 is used to detect the fluorescent emission and in preferred embodiments, may be linked to the electronic control 20 for analysis. Optical filters, e.g., 14, can be placed between the sensor 13 and the detector 15 for wavelength selection. Other optical components may also be utilized, e.g., mirrors, collimating and/or focusing lenses, beam splitters, etc. Optical fibers can be used to deliver selected wavelengths to the sensor and to deliver the fluorescence emission from the sensor to the detector. The light source and the detector may be controlled by electronic control 20 such as a computer.

One embodiment of this invention provides a method for measuring pH and polyhydroxyl compound concentration with a single fluorescent dye. Measurements can be carried out in vitro or in vivo. It may be necessary to calibrate the sensor prior to performing the first measurement. This may be done by first acquiring the absorbance spectra of the sensor at various pHs to determine the wavelengths where isobestic point and absorption maxima for acid and base forms occur and then acquiring the emission signals from at least two of these wavelengths at at least one known pH and glucose concentration.

For the pH and polyhydroxyl concentration measurements, the sensor 13 is first placed in contact with a sample. The sensor 13 is then irradiated at the first excitation wavelength followed by the second excitation wavelength. The first and second excitation wavelengths are typically chosen near the wavelength of the absorption maximum for the acidic form of the fluorescent dye ($\lambda_{acid}$), the wavelength of the absorption maximum for the basic form of the fluorescent dye ($\lambda_{base}$), or the wavelength of the isobestic point ($\lambda_{iso}$), or other selected wavelength. The ratio of the emissions from the first and second excitation wavelengths are used to determine the sample pH. Either the first or second emission, once corrected for pH, can be used to determine the sample glucose concentration.

In variations to the sensing device shown in FIG. 1, the detector may be a standard photodiode detector. There may be two diode detectors, one for a reference and one for the emission signal. Instead of diode detectors, the optical fiber carrying sensor output (fluorescent emission and/or reflected excitation light) may provide input directly to a spectrophotometer or microspectrometer. In a preferred embodiment, the detector comprises a microspectrometer such as the UV/VIS Microspectrometer Module manufactured by Boehringer Ingelheim.

Figure 2:
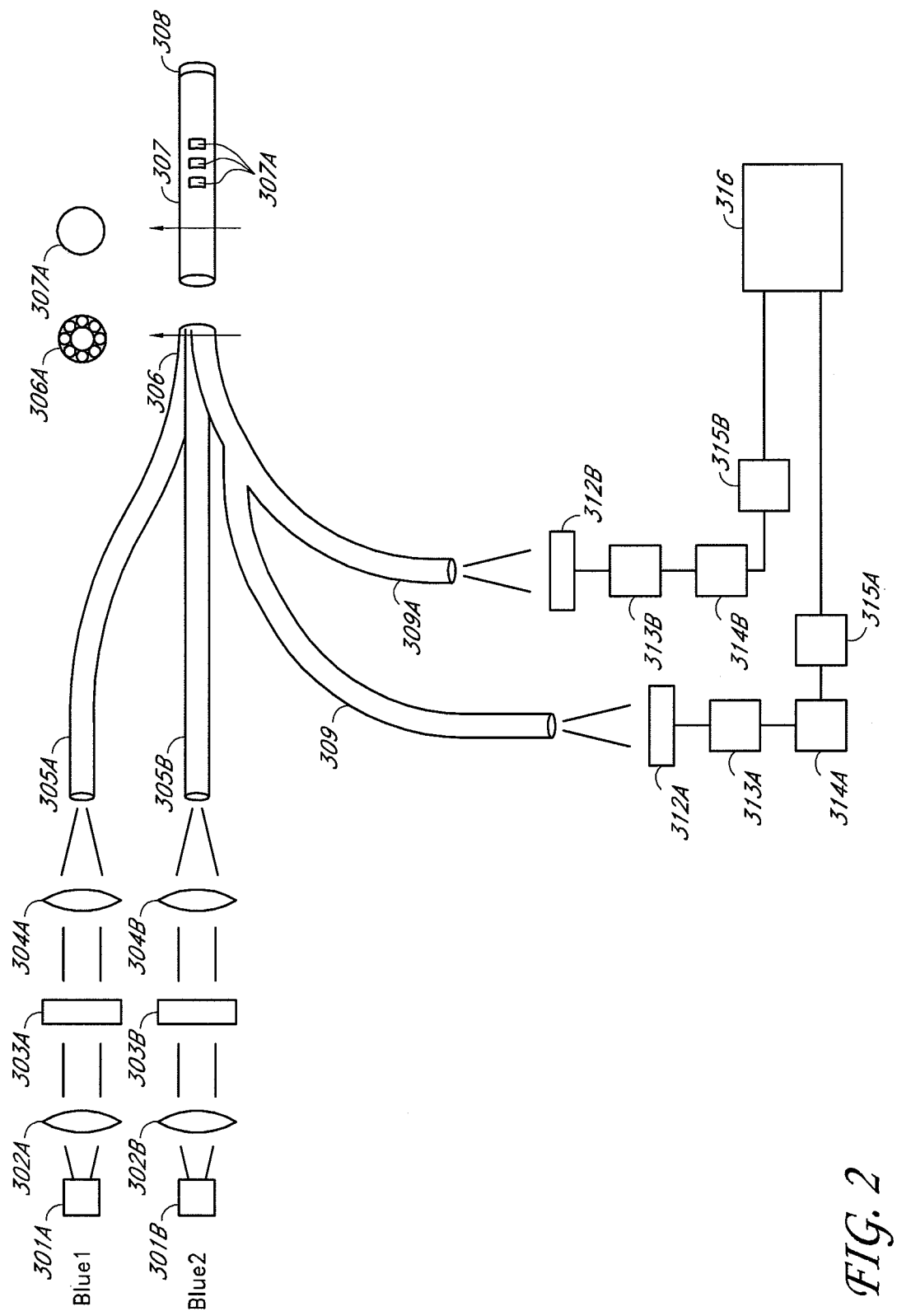
FIG. 2 shows a glucose and pH sensor and optical system comprising two excitation light sources and two detectors in accordance with one preferred embodiment of the present invention.

FIG. 2 shows one embodiment of an optical system that may be used in accordance with preferred aspects of the present invention. With reference to FIG. 2, certain embodiments comprise at least two light sources, 301A and 301B. The light sources generate excitation light that may be transmitted (as illustrated) through collimator lenses 302A and 302B. In certain embodiments, the resulting light from collimator lenses may be transmitted (as illustrated) to interference filters 303A and 303B. In certain embodiments, the resulting light from interference filters may be focused (as illustrated) by focusing lenses 304A and 304B into fiber optic lines 305A and 305B. In certain embodiments, fiber optic lines merge into a single fiber 306 that is continuous with the sensor 307, having the imbedded indicator system 307A. The cross-sections of the fibers may vary (as illustrated) from a bundle of fibers surrounding a central optical fiber 306A to a single fiber 307A.

In certain embodiments (as illustrated), the emission light signals generated by the indicator system 307A as well as the excitation light signals are reflected by mirror 308 and transmitted back out of the sensor into the fiber optic outlet lines 309 and 309A. In the illustrated system, the outlet lines are augmented by including two interference filters 312A, 312B and two detectors 313A, 313B. In preferred embodiments, the interference filter 312A is configured to block the excitation light and allow the emission light to pass to detector 313A where the emission light is detected. In certain embodiments, the signal produced by the detector 313A is amplified by the amplifier 314A and converted into a digital signal by analog-to-digital converter 315A and transmitted to computer 316. In certain embodiments, the interference filter 312B is configured to block the emission light and allow the excitation lights to pass to detector 313B where the excitation light is measured. In certain embodiments, the signal produced by the detector 313B is amplified by the amplifier 314B and converted into a digital signal by analog-to-digital converter 315B and transmitted to computer 316. Ratiometric calculations may be employed to substantially eliminate or reduce non-glucose related factors affecting the intensity of the emission light; these methods are disclosed in detail in co-pending U.S. Provisional Application No. 60/888,477, entitled "Optical systems and methods for ratiometric measurement of glucose using intravascular fluorophore sensors," filed herewith on the same day, and incorporated herein in its entirety by reference thereto.

EXAMPLES

Example 1

Figure 3:
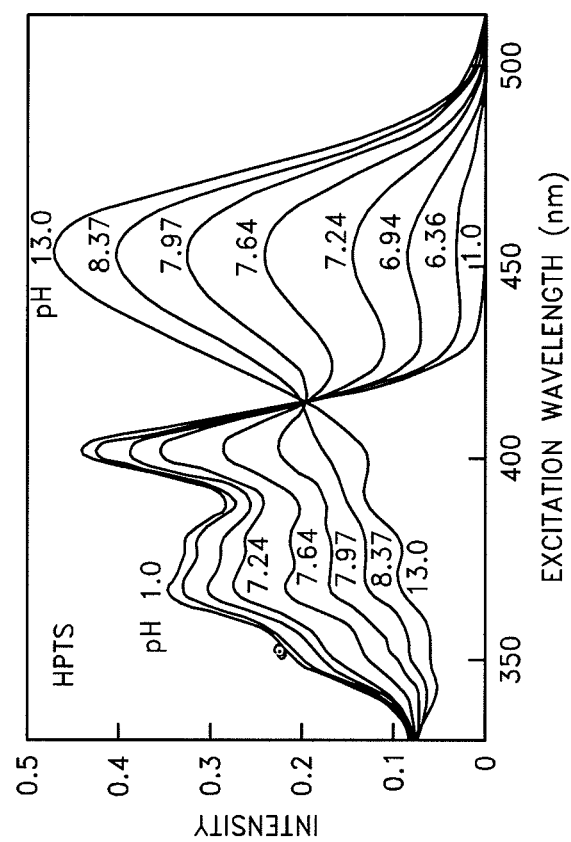
FIG. 3 shows the absorption spectra of HPTS at different pHs.

FIG. 3 shows an example of the excitation/absorption spectrum of a fluorescent dye, in this case HPTS. From the absorption spectra of the fluorescent dye acquired at different pHs, $\lambda_{acid}$, $\lambda_{base}$ and $\lambda_{iso}$ can be determined. At a lower pH (e.g., more acidic condition), the peak at around 405 nm is higher than the peak at around 460 nm, and is therefore the absorption maximum for the acidic form of the fluorescent dye. At a higher pH (e.g., more basic condition), the peak at round 460 nm is higher than the peak at around 405 nm, therefore is the absorption maximum for the basic form of the fluorescent dye. The $\lambda_{iso}$ would be the wavelength where the absorption is independent of the pH, and it would be, for example, around 422 nm for HPTS.

The first fluorescence emission intensity ($I_x$, which could be $I_{acid}$, $I_{base}$ or $I_{iso}$) at a emission wavelength, resulting from the irradiation at the first excitation wavelength (e.g., $\lambda_{acid}$, $\lambda_{base}$ or $\lambda_{iso}$), is then measured by the detector and the result is stored in the electronic control. Then the sensor is again irradiated at the second excitation wavelength. The second excitation wavelength is different from the first excitation wavelength and can also be selected from $\lambda_{acid}$, $\lambda_{base}$ or $\lambda_{iso}$. The detector will then detect/measure the second fluorescence emission intensity ($I_y$, which could be $I_{acid}$, $I_{base}$ or $I_{iso}$) resulting from the irradiation at the second excitation wavelength (e.g., $\lambda_{acid}$, $\lambda_{base}$ or $\lambda_{iso}$). The ratio of the first and the second fluorescence emissions ($I_x/I_y$) can then be computed. Since the $I_x/I_y$ is independent from the polyhydroxyl concentration, a pH standard curve ($I_x/I_y$ vs. pH) can be plotted without considering the effect of polyhydroxyl concentration.

Example 2

(HPTS/MABP4)

Figure 4:
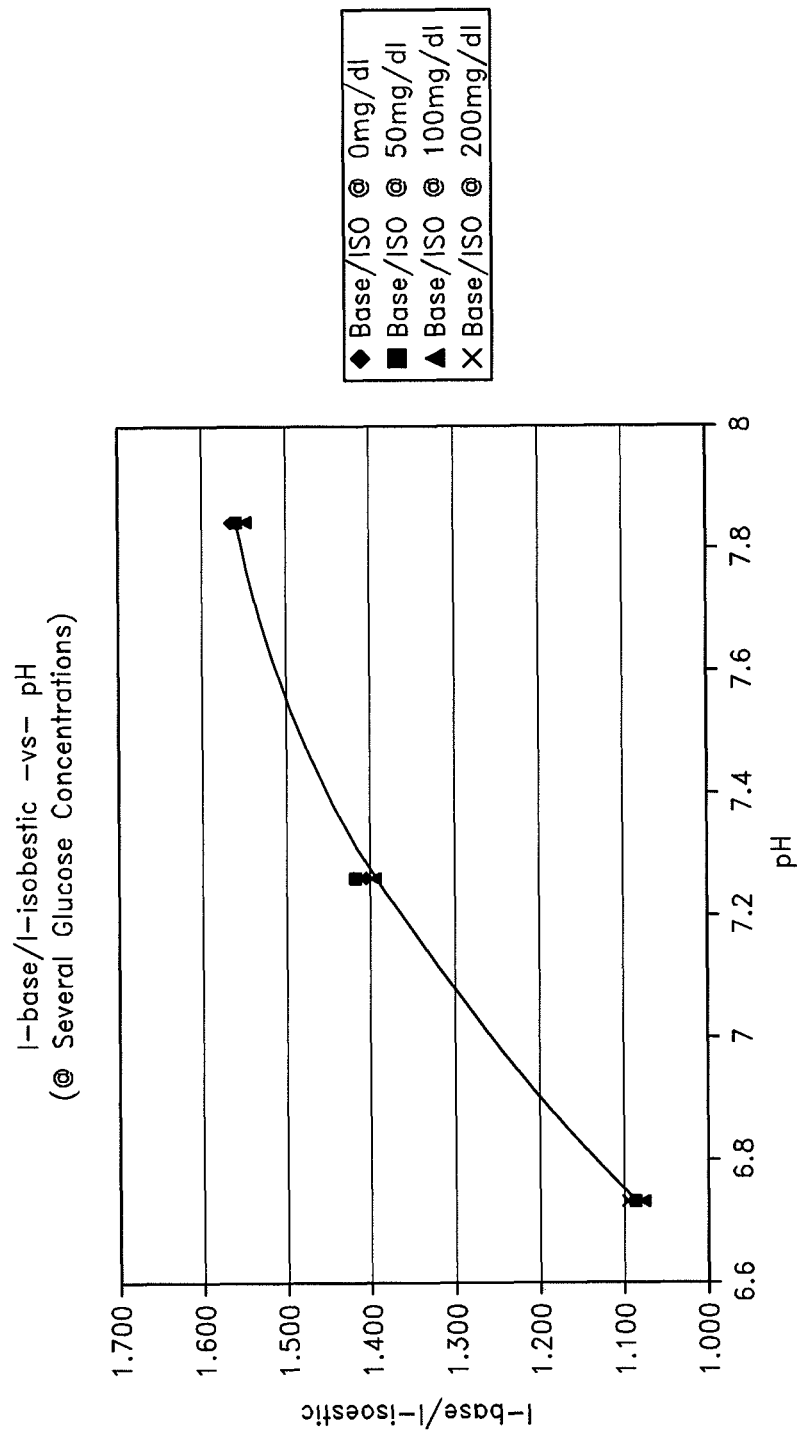
FIG. 4 shows independence of ratiometric pH sensing using HPTS/MABP4 using the $I_{(base)}/I_{(iso)}$ ratio from glucose concentration. The data are plotted as a ratio of the fluorescence emission for corresponding to excitation at 454 nm (base) and 422 nm (isobestic point) vs. pH in various glucose concentrations.

FIG. 4 shows independence of ratiometric pH sensing using HPTS/MABP4 using the $I_{(base)}/I_{(iso)}$ ratio from glucose concentration. The structure of MABP4 is:

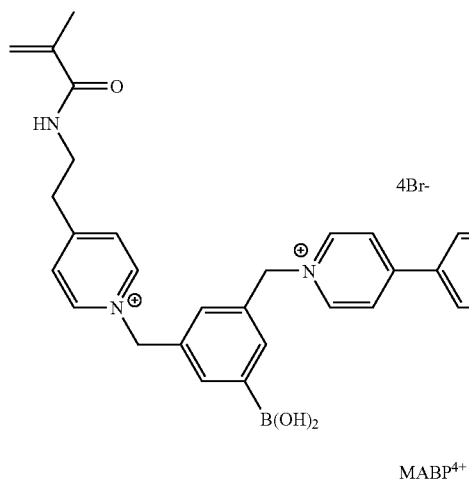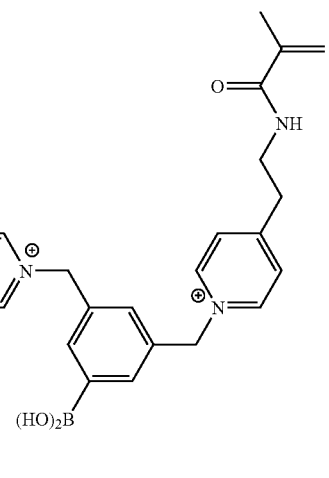

MABP<sup>4+</sup>

The data are plotted as a ratio of the fluorescence emission for corresponding to excitation at 454 nm (base) and 422 nm (isobestic point) vs. pH in various glucose concentrations. The changes in glucose concentrations have no discernable effects on the value of $I_{base}/I_{iso}$ at each specific pH. Thus the pH of the sample can be measured using a standard curve of $I_x/I_y$ vs. pH, regardless of the polyhydroxyl compound concentration in the sample. By correlating or comparing the measured $I_x/I_y$ to the standard curve, one may determine the pH of the sample being measured.

Figure 5:
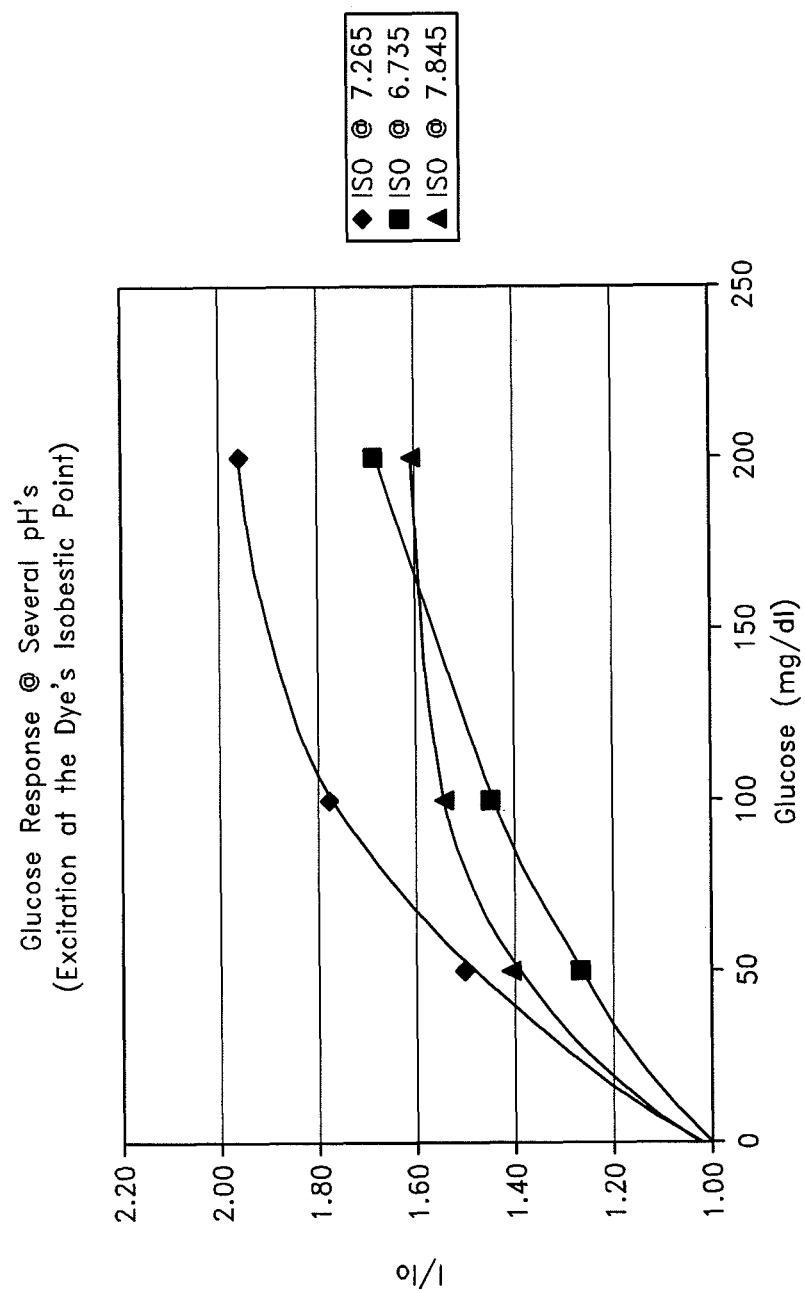
FIG. 5 shows glucose response curves for HPTS/MABP4 excited at 422 nm (isobestic point) at different pHs.

FIG. 5 shows glucose response curves for HPTS/MABP4 excited at 422 nm (isobestic point) at different pHs. By plotting the ratio of $I_x/I_y$ at various glucose levels (I) to $I_x/I_y$ at zero glucose concentration ($I_0$) vs. glucose concentration, a standard polyhydroxyl response curve can be used to determine the glucose concentration in a sample from measured $I/I_0$ values. However, since $I/I_0$ value is dependent on the pH of the sample, the standard glucose response curve can be affected by the different pH. To circumvent this, several standard glucose response curves at different pHs within the physiological range can be plotted and available for selection by either the electronic control or the operator of the sensor device. When the $I_x/I_y$ measurement of the sample is available, the electronic control or the operator would know the pH of the sample from the standard $I_x/I_y$ vs. pH curve, and the correct standard polyhydroxyl response curve (e.g., glucose response curve) may be used for determining the accurate glucose concentration. Although the examples shown in the figures concern determination of glucose concentration, the application of the method and device of the present invention is not limited to detecting glucose concentration. Since the fluorescent system responds to polyhydroxyl compounds the same way it responds to glucose, the sensor device can be used to detect any polyhydroxyl compound concentration and the pH at the same time.

Example 3

(SNARF-1)

Figure 6:
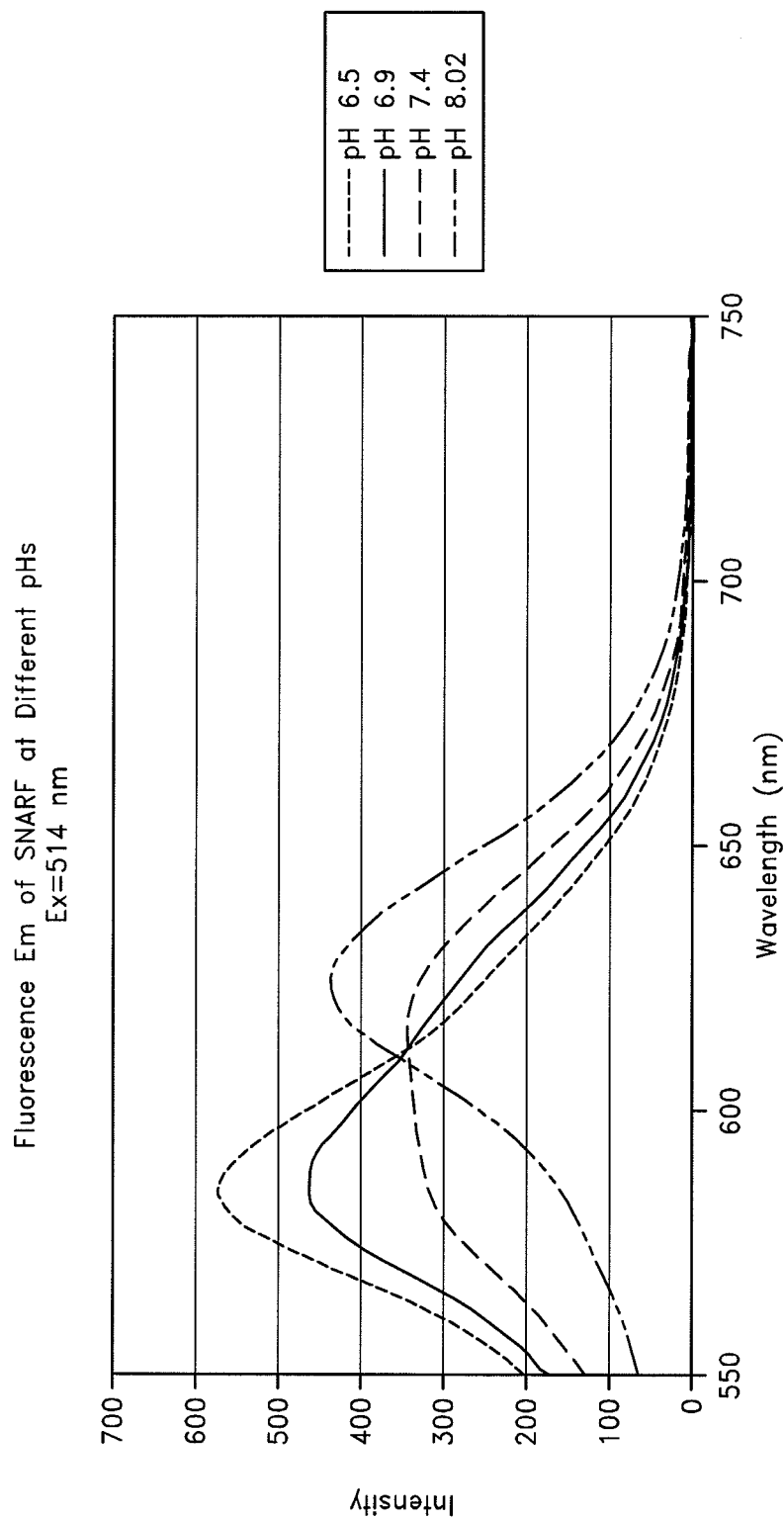
FIG. 6 shows the absorption spectra of SNARF-1 at different pHs in solution.
Figure 7:
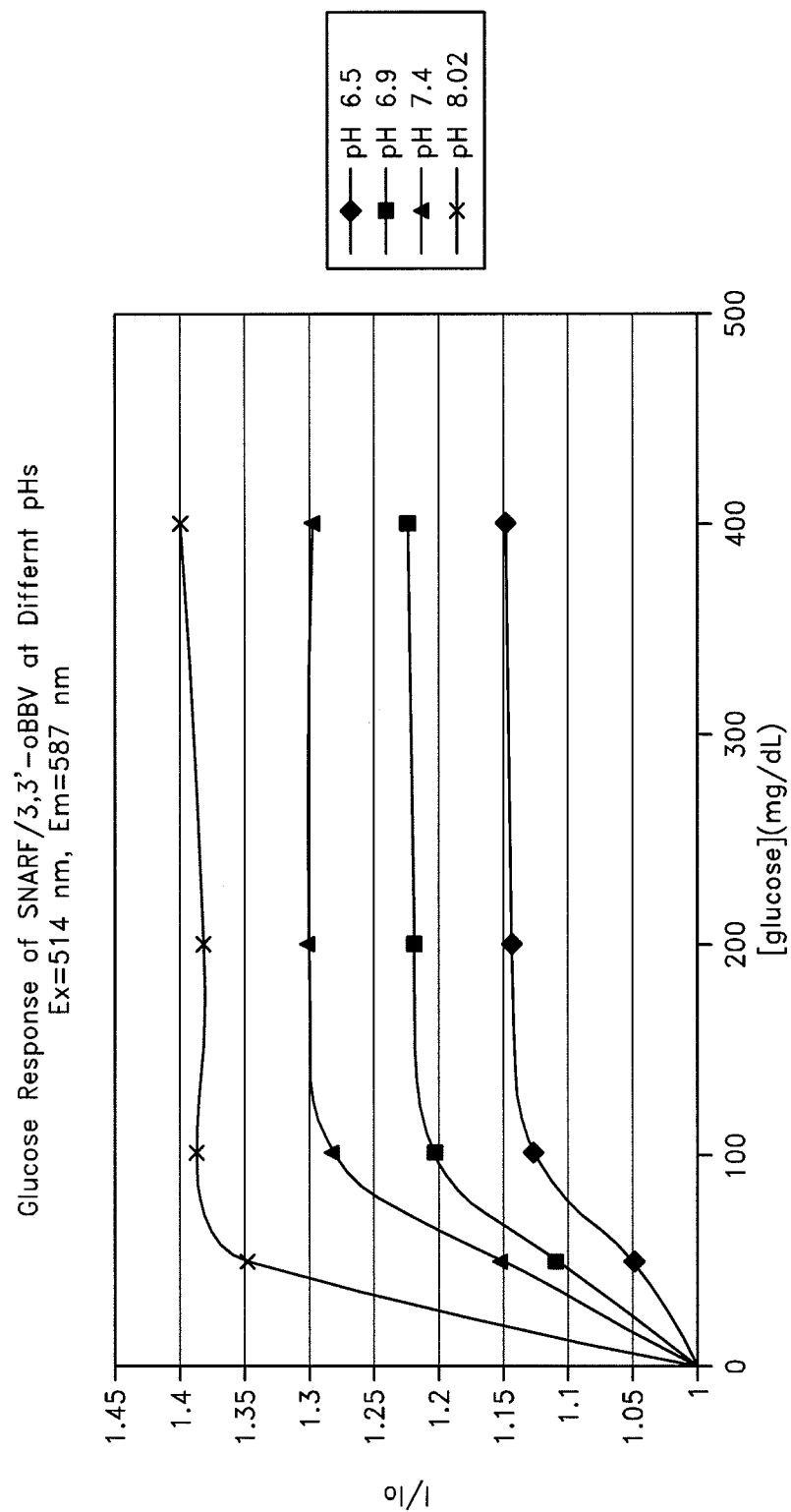
FIG. 7 shows glucose response curves. for SNARF-1/3,3'-oBBV in solution at different pHs excited at 514 nm/emission at 587 nm.
Figure 8:
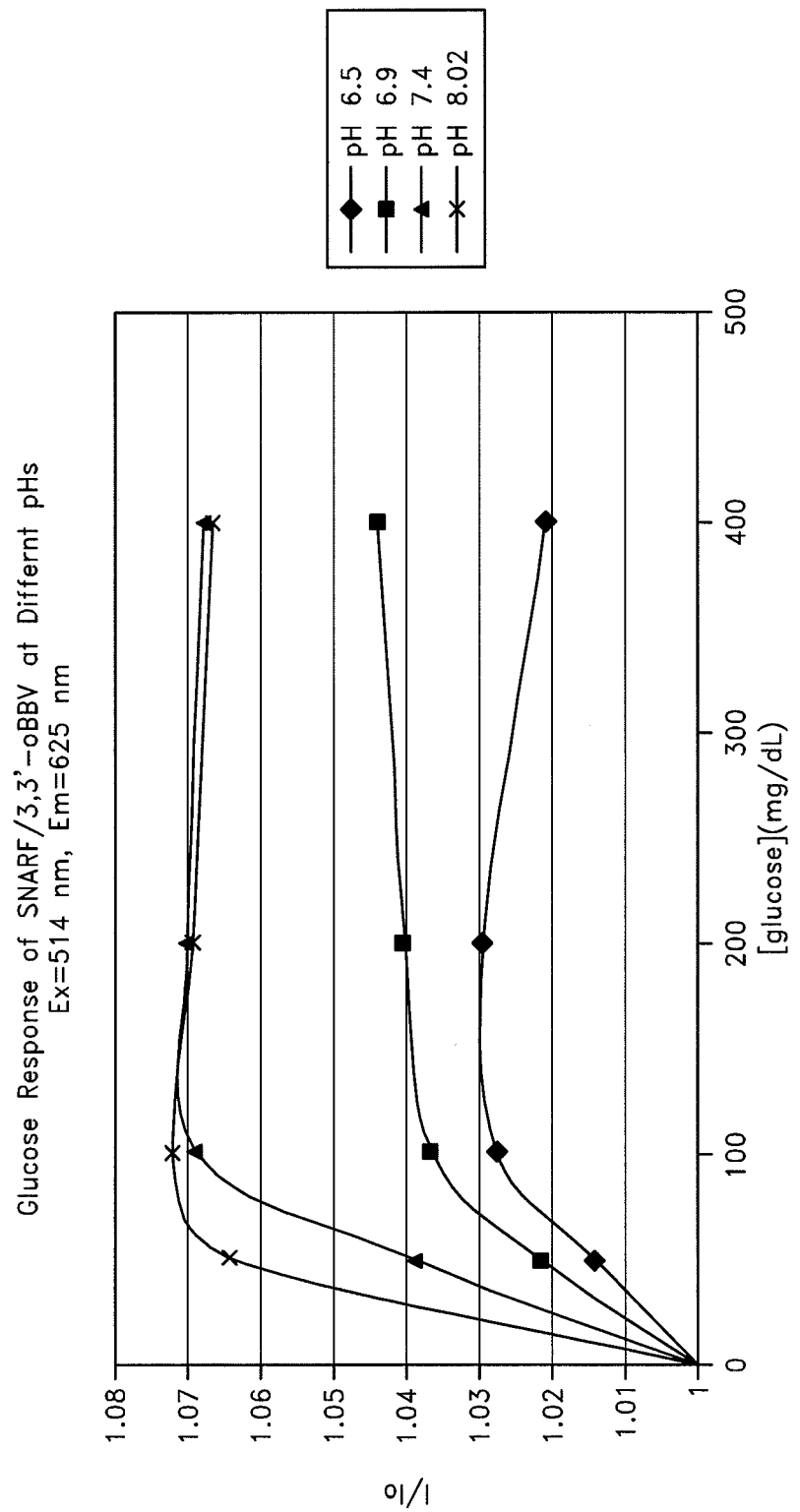
FIG. 8 shows glucose response curves for SNARF-1/3,3'-oBBV in solution at different pHs excited at 514 nm/emission at 625 nm.
Figure 9:
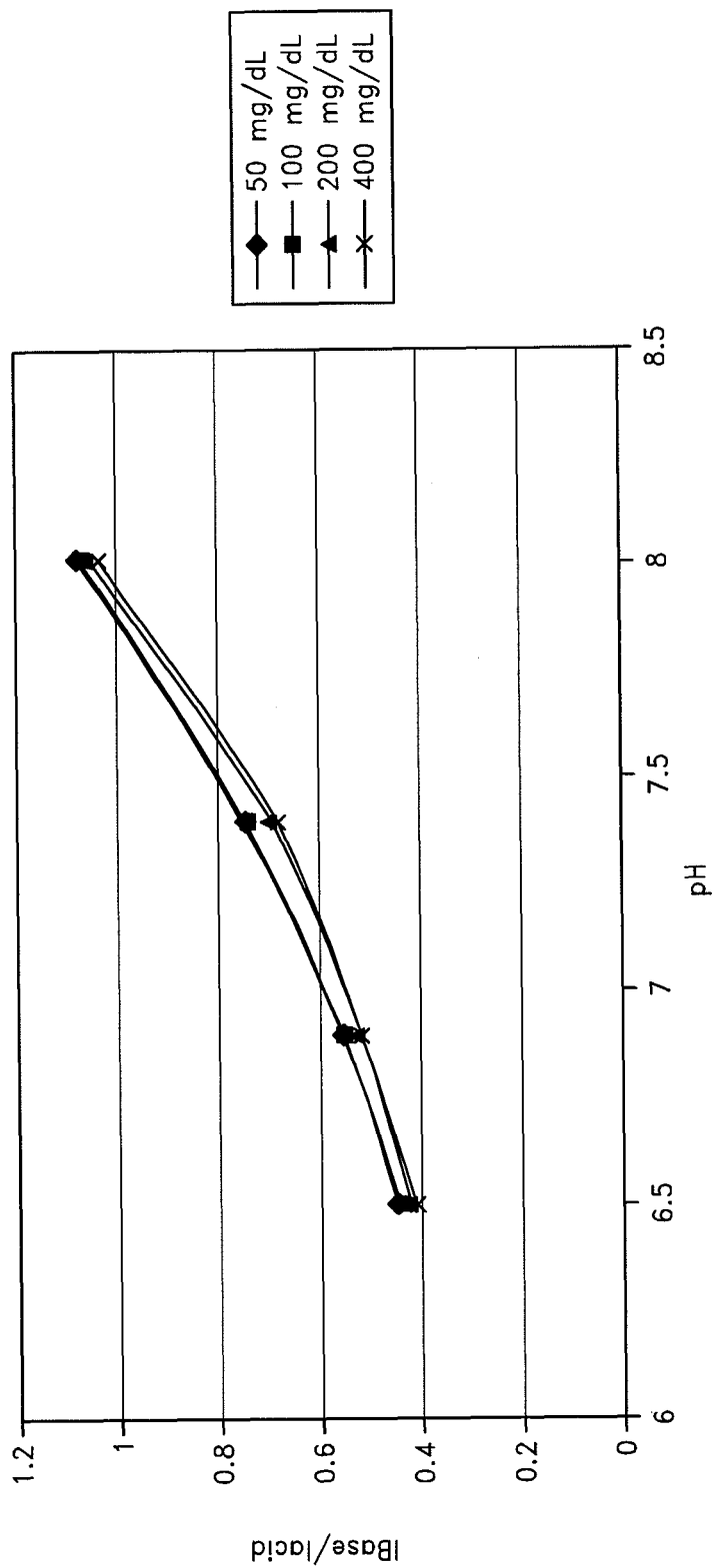
FIG. 9 shows ratiometric sensing of pH at different glucose concentrations with SNARF-1/3,3'-oBBV in solution using the $I_{(base)}/I_{(acid)}$ ratio.

FIG. 6 shows the absorption spectra of SNARF-1 at different pHs in solution. SNARF is a tradename for a class of commercial dyes from Molecular Probes, Inc. These experiments were carried out using SNARF-1. FIGS. 7 and 8 show glucose response curves for SNARF-1/3,3'-oBBV in solution at different pHs determined at 514 nm excitation/587 nm emission (FIG. 7), or at 514 nm excitation/625 nm emission (FIG. 8). FIG. 9 shows ratiometric sensing of pH at different glucose concentrations with SNARF-1/3,3'-oBBV in solution using the $I_{(base)}/I_{(acid)}$ ratio determined at a single excitation wavelength of 514 nm and emission wavelengths of 587 and 625 nm. Thus, the dual-dual dye SNARF-1 may be used operably coupled to the quencher 3,3'-oBBV (in solution) as a single exciter-dual emitter fluorophore to determine both pH ratiometrically and glucose.

Example 4

(HPTS-triLysMA/3,3'-oBBV/DMAA)

Figure 10:
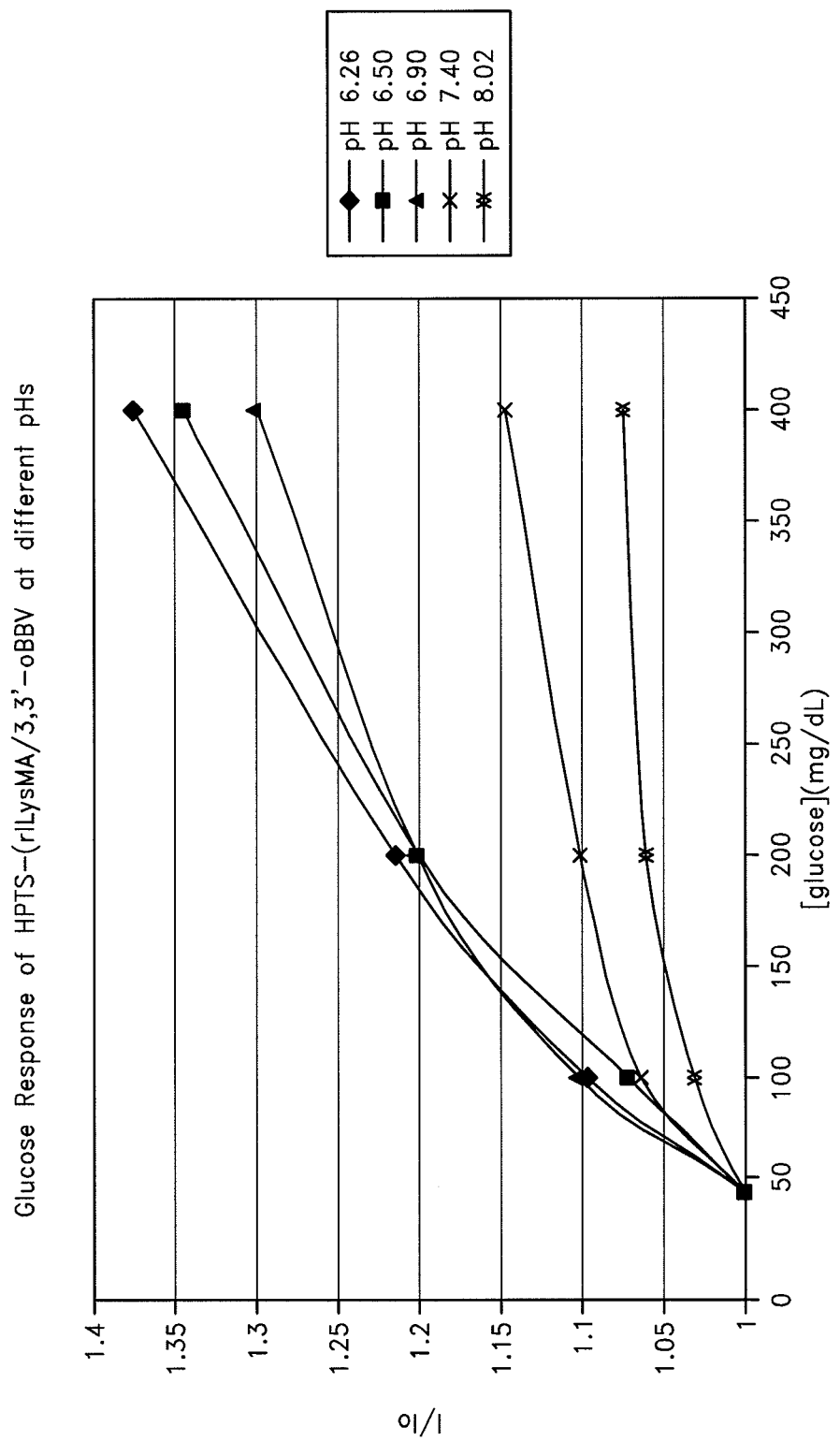
FIG. 10 shows glucose response curves for HPTS-triLysMA/3,3'-oBBV/DMAA at different pHs.
Figure 11:
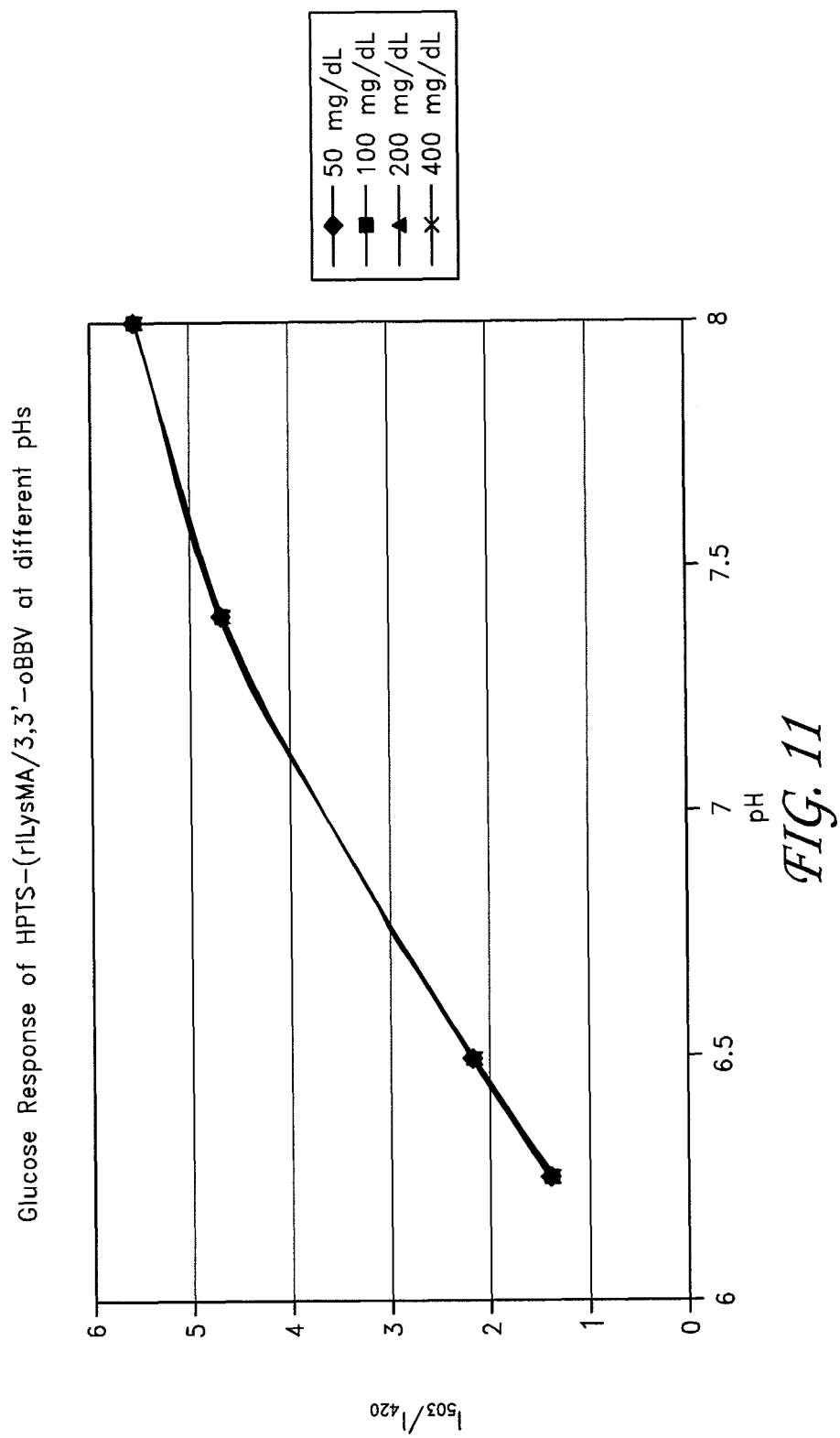
FIG. 11 shows ratiometric sensing of pH at different glucose concentrations using HPTS-triLysMA/3,3'-oBBV/DMAA, using the $I_{(base)}/I_{(acid)}$ ratio.

FIG. 10 shows the glucose response of HPTS-triLysMA/3,3'-oBBV/DMAA indicator system at different pHs. FIG. 11 shows ratiometric sensing of pH at different glucose concentrations with the HPTS-triLysMA/3,3'-oBBV/DMAA indicator system, using the $I_{(base)}/I_{(acid)}$ ratio. It can be seen that this indicator system provides a linear pH curve over the physiologic pH range.

Example 5

(HPTS-triCysMA/3,3'-oBBV/DMMA)

Figure 12:
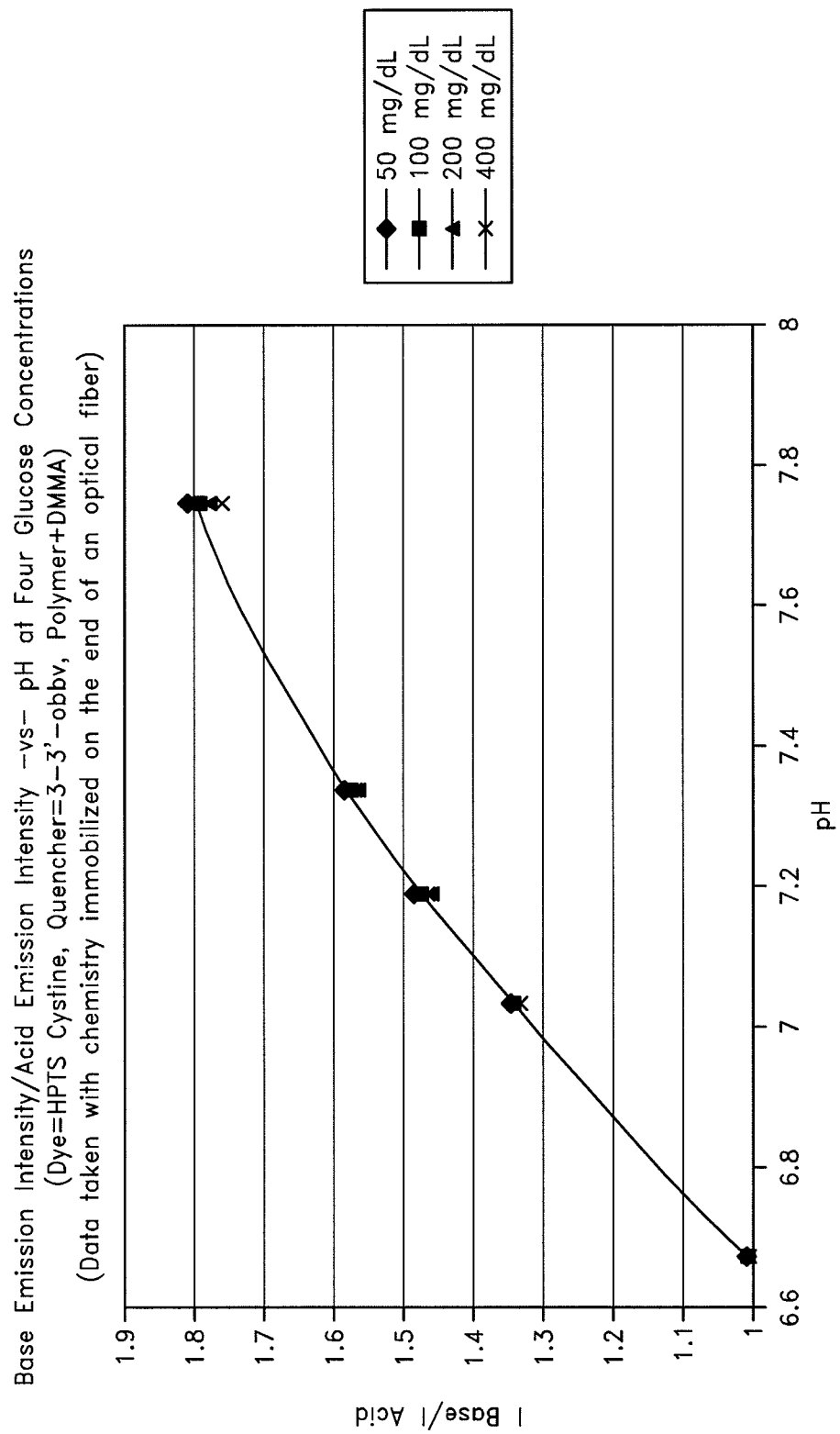
FIG. 12 shows ratiometric sensing of pH at different glucose concentrations using HPTS-triCysMA/3,3'-oBBV/DMMA wherein the indicator system is immobilized on the end of an optical fiber, using the $I_{(base)}/I_{(acid)}$ ratio.

FIG. 12 shows ratiometric sensing of pH at different glucose concentrations with the HPTS-triCysMA/3,3'-oBBV/DMMA indicator system, using the $I_{(base)}/I_{(acid)}$ ratio. It can be seen that this indicator system provides a linear pH curve over the physiologic pH range. For this example, the indicator system was immobilized in a hydrogel embedded at the end of an optical fiber. The acid and base emission signals were measured using a hand-held detector.

Lifetime Chemistry

In another preferred embodiment, glucose concentrations can be determined by exploiting the phenomena of fluorescence resonance energy transfer (FRET). FRET is the transfer of energy from a donor fluorophore to an acceptor molecule.

FRET occurs when the donor fluorophore, which fluoresces at a wavelength absorbed at least in part by the acceptor molecule, is in close proximity to the acceptor such that the donor fluorophore can transfer energy to the acceptor through molecular interactions. The fluorescence lifetime of the fluorophore, where the fluorescence lifetime is the time the fluorophore remains in the excited state, is altered by FRET. Thus, measuring the fluorescence lifetime of the fluorophore allows one to determine whether the fluorophore is bound to the acceptor.

Lifetime can be measured by using a time-domain method where the fluorophore is excited by a brief pulse of excitation light and the fluorescence intensity is measured over time. The excitation pulse can be a pulse from a laser with a duration in the picoseconds range up to a duration of about a few nanoseconds. In other embodiments, the pulse duration can be greater than about a few nanoseconds. The fluorescence intensity of the fluorophore as a function of time is given by the equation:

$$I(t) = I_0 * \exp(-t/\tau) \quad \text{Equation 1}$$

Figure 13:
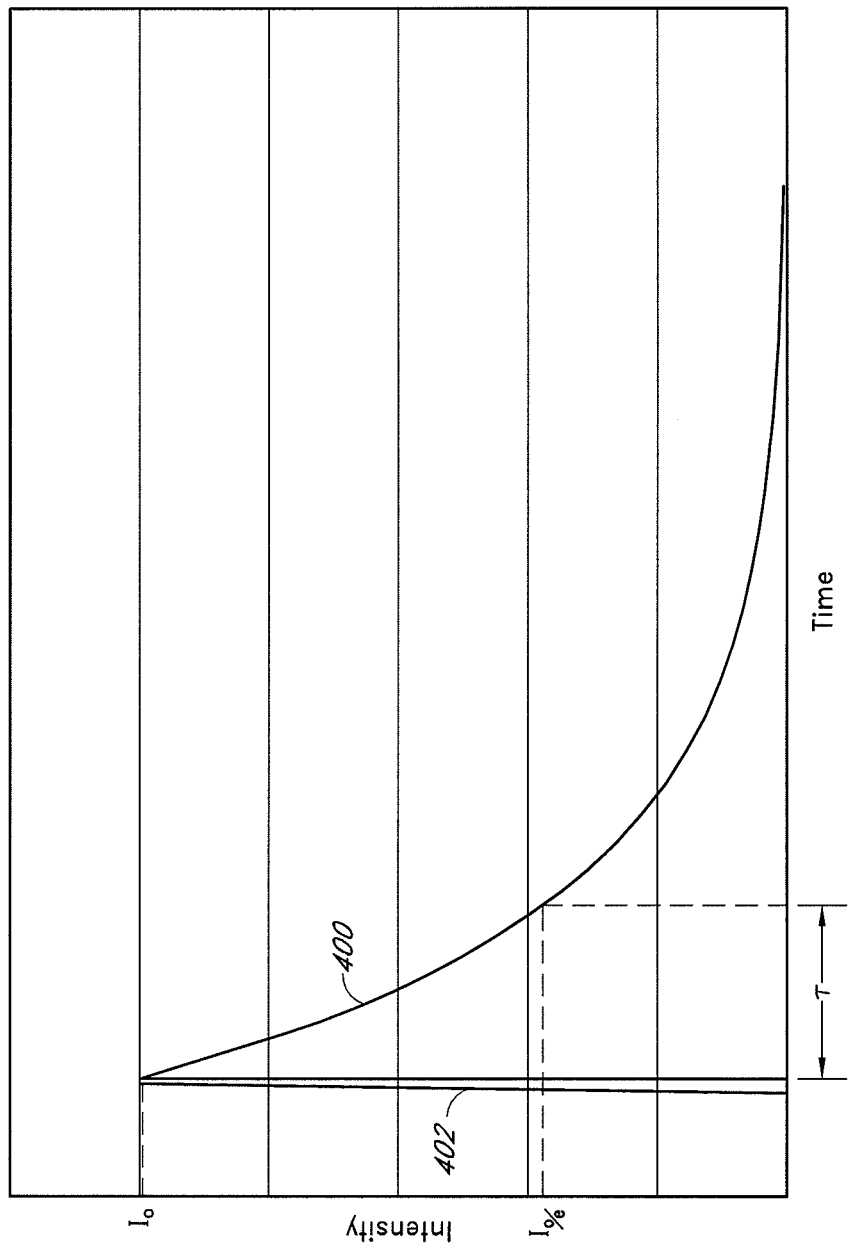
FIG. 13 shows a graph of the decay of fluorescence intensity over time after a fluorophore is subjected to a pulse of excitation light.

I(t) is the fluorescence intensity at time (t), $I_0$ is the initial intensity after excitation and $\tau$ is the fluorescence lifetime which is defined as the time required for I(t) to decay to $I_0/e$. Equation 1 is applicable to a fluorophore with a single exponential decay of fluorescence and a lifetime that is substantially longer than the excitation pulse. FIG. 13 shows a graph of the decay of the fluorescent emission 400 over time after a pulse of excitation light 402. The time it takes the initial intensity, $I_0$, to drop to $I_0/e$ is equal to the lifetime, $\tau$.

An alternative method of measuring lifetime is by a frequency-domain method where the fluorophore is excited by a frequency modulated excitation light. The fluorescence lifetime, $\tau$, can be determined by measuring the phase shift of the emission from the fluorophore relative to the excitation light, or by measuring the modulation ratio, using the following equations:

$$\tau_\phi = \omega^{-1} * \tan(\phi) \quad \text{Equation 2}$$

$$\omega = 2\pi f \quad \text{Equation 3}$$

$$\tau_M = \omega^{-1} * (M^{-2} - 1)^{1/2} \quad \text{Equation 4}$$

$$M = \frac{(AC/DC)_{EM}}{(AC/DC)_{EX}} \quad \text{Equation 5}$$

Figure 14:
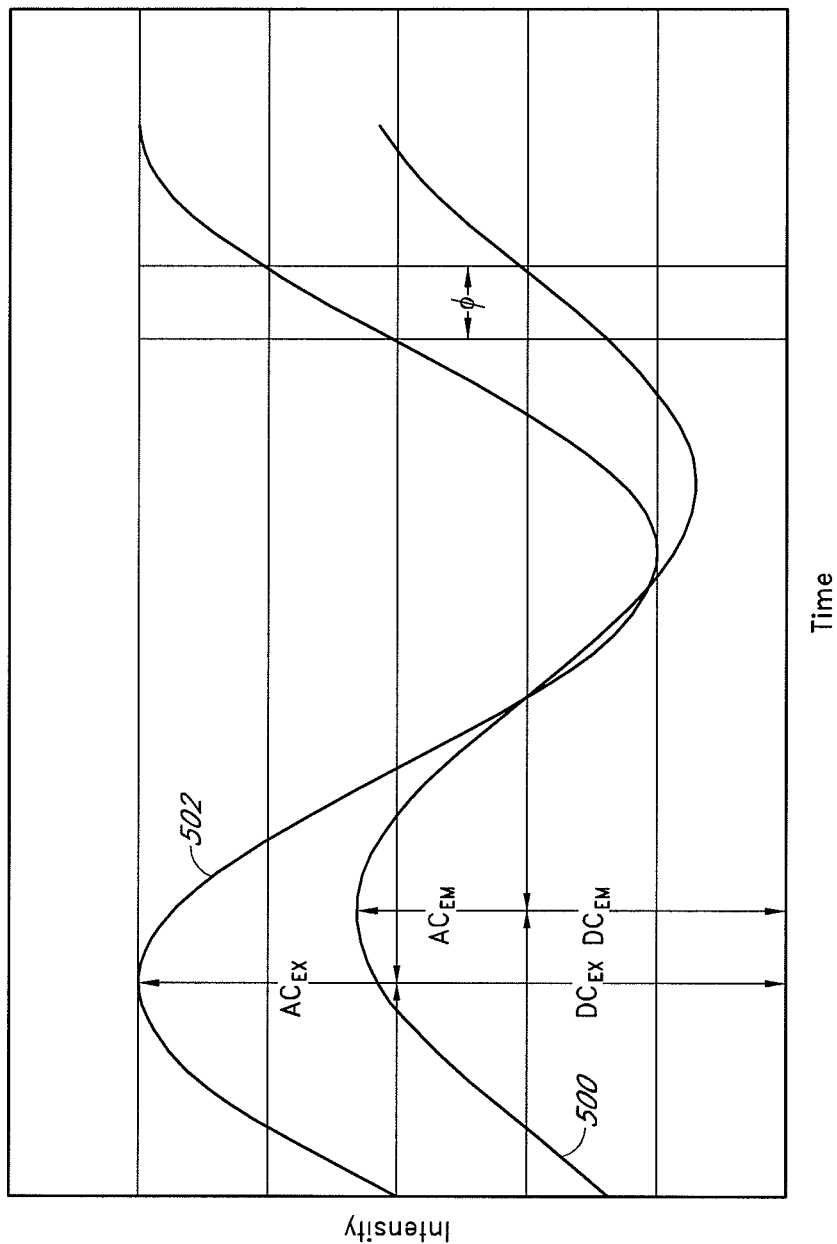
FIG. 14 shows a graph of the emission signal resulting from a frequency modulated excitation signal.

$\tau_\phi$ is the lifetime determined by measuring the phase shift, $\phi$. $\omega$ is the angular frequency of the frequency modulated excitation light and $f$ is the linear frequency. $\tau_M$ is the lifetime determined by measuring the modulation ratio, M. AC is the magnitude of the alternating portion of the signal, or the amplitude of the wave, while DC is the amplitude of the DC portion of the signal. EM refers to the emission signal, and EX refers to the excitation signal. FIG. 14 is a graph showing the relationship between the emission signal 500 and the excitation signal 502 and the variables described in Equations 2-5.

Preferred binding assay configurations for use in the sensor include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g. Fab fragments), lectins (e.g. concanavalin A), hormone receptors, drug receptors, aptamers and molecularly-imprinted polymers. Preferably the analyte analog should be a substance of higher molecular weight than the analyte such that it cannot freely diffuse out of the sensor. For example, an assay for glucose might employ a high molecular weight glucose polymer such as dextran as the analyte analog.

Suitable optical signals which can be used as an assay readout in accordance with the invention include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance.

In some preferred embodiments of the sensor of the invention incorporates a competitive, reagent limited binding assay which generates an optical readout using the technique of fluorescence resonance energy transfer. In this assay format the analyte analog is labelled with a first chromophore and the analyte binding agent is labelled with a second chromophore. One of the first and second chromophores acts as a donor chromophore and the other acts as an acceptor chromophore. It is an important feature of the assay that the fluorescence emission spectrum of the donor chromophore overlaps with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as FRET, with the result that a proportion of the fluorescent signal emitted by the donor chromophore is quenched and, in some instances, that the acceptor chromophore emits fluorescence. Fluorescence resonance energy transfer will generally only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore) as labelled analyte analog is displaced from binding to the analyte binding agent. The intensity or lifetime of the fluorescent signal emitted from the donor chromophore thus correlates with the concentration of analyte in the fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to replace the sensor. As the sensor degrades, the amount of acceptor chromophore present in the sensor will decrease and hence the intensity of fluorescent signal detected upon excitation of the acceptor chromophore will also decrease. The fall of this signal below an acceptable baseline level would indicate the need to implant or inject a fresh sensor. Competitive binding assays using the fluorescence resonance energy transfer technique which are capable of being adapted for use in the sensor of the invention are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp21-30) describe a homogeneous assay method for the measurement of glucose based on fluorescence resonance energy transfer between a labelled glucose analog (FITC labelled dextran) and a labelled glucose binding agent (rhodamine labelled concanavalin A). In all of these configurations the acceptor and donor chromophores/quenchers can be linked to either the binding agent or the analyte analog.

Fluorescence lifetime or fluorescence intensity measurements may be made. As described in Lakowitz et al, Analytica Chimica Acta, 271, (1993), 155-164, fluorescence lifetime may be measured by phase modulation techniques.

Figure 15A:
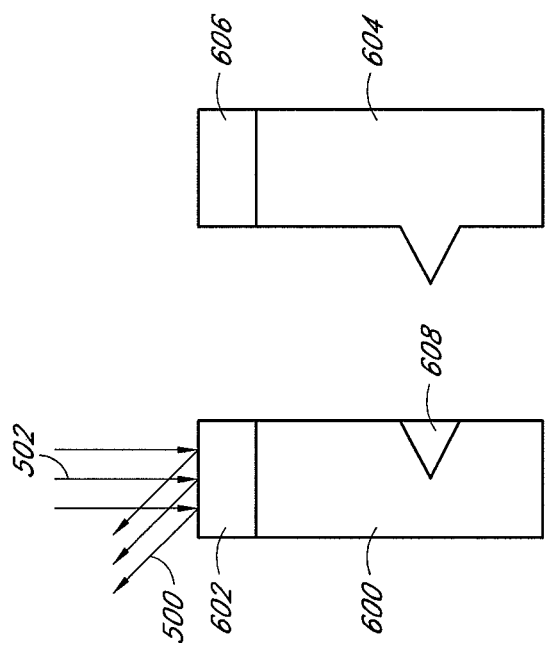
FIGS. 15A-C show the interaction between a glucose binding molecule linked to a fluorophore, a glucose analog linked to an acceptor and a glucose molecule.
Figure 15B:
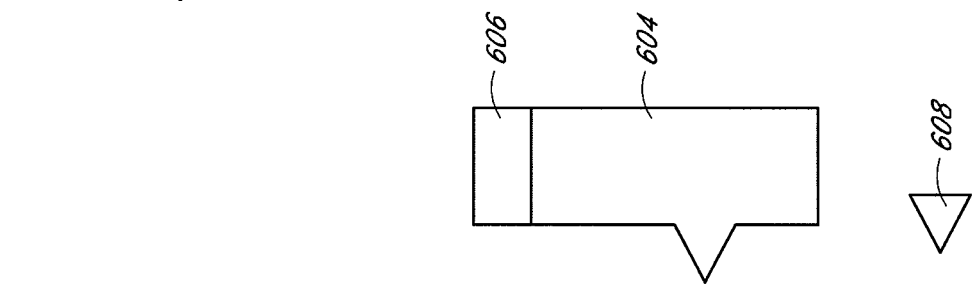
Figure 15C:
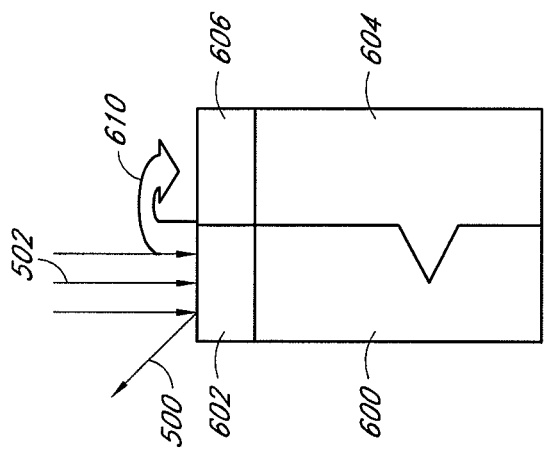

In some preferred embodiments as shown in FIGS. 15A, 15B and 15C, a competitive binding system to measure glucose using FRET comprises a glucose binding molecule 600 linked to a donor fluorophore 602 and a glucose analog 604 linked to an acceptor molecule 606. The glucose binding molecule 600 is capable of binding with both glucose 608 and the glucose analog 604. As shown in FIG. 15A, when the glucose analog 604 is bound to the glucose binding molecule 600, the fluorescent emission 500 from the fluorophore 602 is reduced in magnitude and shifted in phase and lifetime by FRET 610 because the fluorophore 502 is in close proximity to the acceptor 606. In other embodiments, the fluorophore 602 is linked to the glucose analog 604 and the acceptor 606 is linked to the glucose binding molecule 600.

As shown in FIG. 15B, glucose 608 competes with the glucose analog 604 for the binding site on the glucose binding molecule 600. As shown in FIG. 15C, the glucose molecule 608 can displace the glucose analog 604 from the glucose binding molecule 600 so that the acceptor 606 does not alter the emission lifetime 500 of the fluorophore 602 via FRET 610.

In a system where there are a certain concentration of glucose binding molecules, glucose analogs and glucose molecules, an equilibrium will exist between the number of bound glucose molecules to the number of bound glucose analogs. A change in the number of glucose molecules in the system, changes the equilibrium between bound glucose molecules to bound glucose analogs. This in turn changes the mean lifetime of the fluorophore emission.

In some preferred embodiments, the system is excited by a frequency modulated excitation light less than approximately 1 MHz, between approximately 1 to 200 MHZ, or greater than approximately 200 MHz. In some embodiments, the frequency is approximately 0.05, 0.1, 1, 10, 20, 30, 40, 50, 60, 70, 80, 90, 100, 110, 120, 130, 140, 150, 160, 170, 180, 190 or 200 MHz. By measuring the degree of the phase shift of the system, an average FRET induced phase shift for the system can be determined which corresponds to an average lifetime value for the system as defined by Equations 2 and 3 described above. Both the phase shift and the lifetime values can be correlated to the glucose concentration. The magnitude of the phase shift is independent of the amplitude of the emission.

In other preferred embodiments, the system is excited by a pulse and the decay of the fluorescence is measured over time. The lifetime can be determined using Equation 1 described above, and glucose concentration can be correlated to the lifetime value.

In preferred embodiments, the glucose binding molecule with a donor fluorophore and the glucose analog with an acceptor can be substantially immobilized in the hydrogel described above such that diffusion of the glucose binding molecule and the glucose analog out of the hydrogel is substantially reduced. In addition, the sensor is configured to provide excitation light at a wavelength absorbed by the donor fluorophore as described above. In some embodiments, the excitation light is provided as a short pulse from a laser or a light emitting diode (LED). In other embodiments, the excitation light is frequency modulated. In some embodiments, the frequency modulated excitation light is provided by a laser. In some embodiments the frequency modulated excitation light is provided by a LED. The sensor also has a detector that detects the amplitude of the emission over time and/or the phase shift of the emission and/or the amplitudes of the AC and DC portions of the emission and excitation light. The detector can be a photodetector or multiple photodetectors. The excitation and emission light can be transmitted throughout the sensor via optical fibers.

In some embodiments, the sensor can be introduced into a patient's blood vessel, such as a vein, artery or capillary, for measuring the intravascular concentration of an analyte in the patient's blood. In some embodiments, the chemistry used to measure the concentration of the analyte is based on a correlation of fluorescence intensity of a fluorophore to analyte concentration, as described above in more detail. In some embodiments, the chemistry used to measure the concentration of the analyte is based on a correlation of fluorescence lifetime of a fluorophore to analyte concentration, as described above in more detail. In some embodiments, the sensor is used to measure the concentration of glucose.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A sensor for determining glucose concentration comprising: an optical fiber comprising a non-consuming, equilibrium fluorescence chemical indicator system disposed along a distal region of the optical fiber, the chemical indicator system comprising an HPTS-triCysMA fluorophore that generates a fluorescence emission signal when excited by light and a glucose binding moiety in close enough proximity to the fluorophore to interact with the fluorophore and modulate the fluorescence emission signal, wherein the extent of modulation of the fluorescence emission signal by the glucose binding moiety is related to the amount of glucose bound to the glucose binding moiety; a light source; and a detector.

2. The sensor of claim 1, wherein the fluorescence emission signal comprises a fluorescence intensity.

3. The sensor of claim 1, wherein the fluorescence emission signal comprises a fluorescence lifetime.

4. The sensor of claim 1, wherein the light source is a laser.

5. The sensor of claim 1, wherein the light source is a light emitting diode.

6. The sensor of claim 1, wherein the sensor further comprises a hydrogel that substantially immobilizes the glucose binding moiety and the fluorophore and is permeable to glucose.

7. The sensor of claim 1, wherein the sensor further comprises a membrane wherein the glucose binding moiety and the fluorophore are substantially retained within a volume at least partially enclosed by the membrane.

8. A method for determining the glucose concentration comprising: inserting the sensor of claim 1 into a patient; exciting the fluorophore with light; detecting a fluorescence emission signal from the fluorophore; and determining the concentration of glucose.

9. The method of claim 8, wherein the light is a pulse of light.

10. The method of claim 9, further comprising measuring the decay of the fluorescence emission signal over time; and calculating a fluorescence lifetime.

11. The method of claim 8, wherein the light is frequency modulated.

12. The method of claim 11, further comprising measuring the phase shift between the fluorescence emission signal and the light.

13. The method of claim 12, further comprising calculating a fluorescence lifetime.

14. The method of claim 11, further comprising measuring a modulation ratio; and calculating a fluorescence lifetime.

15. The method of claim 8, further comprising measuring the fluorescence intensity of the fluorescence emission signal.

16. The sensor of claim 1, wherein the glucose binding moiety comprises an aromatic boronic acid.

17. The sensor of claim 16, wherein the aromatic boronic acid is coupled to a viologen.

18. The sensor of claim 1, wherein the fluorophore and the glucose binding moiety are not covalently bound to one another.

19. The sensor of claim 1, wherein the fluorophore comprises an acid form that absorbs light at a first excitation wavelength and a base form that absorbs light at a second excitation wavelength, such that a pH-dependent shift in absorption enables dual-excitation ratiometric determination of pH and glucose.

* * * * *